United States Patent
Dai et al.

(10) Patent No.: US 10,179,037 B2
(45) Date of Patent: Jan. 15, 2019

(54) RECIPROCALLY ROTATABLE BRUSH HEAD

(71) Applicant: SHANGHAI SHIFT ELECTRICS CO., LTD., Shanghai (CN)

(72) Inventors: Xiaoguo Dai, Shanghai (CN); Zhenwu Xu, Shanghai (CN); Ling Dai, Shanghai (CN)

(73) Assignee: Shanghai Shift Electrics Co., Ltd., Shanghai (CN)

( * ) Notice: Subject to any disclaimer, the term of this patent is extended or adjusted under 35 U.S.C. 154(b) by 0 days.

(21) Appl. No.: 15/575,747

(22) PCT Filed: May 20, 2015

(86) PCT No.: PCT/CN2015/079351
§ 371 (c)(1),
(2) Date: Nov. 20, 2017

(87) PCT Pub. No.: WO2016/183815
PCT Pub. Date: Nov. 24, 2016

(65) Prior Publication Data
US 2018/0177576 A1 Jun. 28, 2018

(51) Int. Cl.
*A61C 17/34* (2006.01)
*A61C 17/22* (2006.01)
(Continued)

(52) U.S. Cl.
CPC ............ *A61C 17/222* (2013.01); *A46B 13/02* (2013.01); *A61C 17/26* (2013.01); *A61C 17/34* (2013.01); *A46B 2200/1066* (2013.01)

(58) Field of Classification Search
CPC .. A61C 17/34; A61C 17/3481; A61C 17/3427
See application file for complete search history.

(56) References Cited

U.S. PATENT DOCUMENTS

| | | | |
|---|---|---|---|
| 8,887,338 B1 | 11/2014 | Brar | |
| 2015/0202031 A1* | 7/2015 | Dai | A61C 17/3418 15/22.1 |

FOREIGN PATENT DOCUMENTS

| | | |
|---|---|---|
| CN | 2652351 Y | 11/2004 |
| CN | 201710491 U | 1/2011 |

(Continued)

OTHER PUBLICATIONS

International Patent Application No. PCT/CN2015/079351; Int'l Search Report; dated Feb. 25, 2016; 3 pages.

*Primary Examiner* — Michael Jennings
(74) *Attorney, Agent, or Firm* — Baker & Hostetler LLP

(57) ABSTRACT

A brush head for performing reciprocating rotation comprises a driving wheel and a housing on which a top hole and/or a central through hole are/is distributed in a centering manner. The center line(s) of the holes and a rotation axis (L1) of a driving shaft are located at a same line, and the driving shaft penetrates through the central through hole. The fitted region of the driving shaft and the driving wheel enters the through holes distributed on the driving wheel to link the driving shaft and the driving wheel fixedly. A driven part matching a driving part is distributed on a protrusion of the brush disc on which a hollow region is formed. The driving shaft penetrates through or enters the hollow region and limits the brush disc to move. The brush disc is incapable of performing reciprocating rotation when the driving shaft is not installed or is damaged.

40 Claims, 16 Drawing Sheets

(51) Int. Cl.
   *A61C 17/26* (2006.01)
   *A46B 13/02* (2006.01)

(56) References Cited

FOREIGN PATENT DOCUMENTS

| CN | 202113181 U | 1/2012 |
| CN | 202875521 U | 4/2013 |
| CN | 103654987 A | 3/2014 |
| CN | 104825243 A | 8/2015 |
| CN | 204798047 U | 11/2015 |

\* cited by examiner

RECIPROCALLY ROTATABLE BRUSH HEAD

TECHNICAL FIELD

The present invention relates to a brush head, and more specifically, to a reciprocally rotatable brush head capable of preventing the carrier from disengaging from the head, which is small in size, simple in structure and easy to assemble.

BACKGROUND

In the utility model patent CN 2614048Y assigned to the inventor of the present invention, there is disclosed an electric toothbrush having a bristle holder of the brush head mounted in a mounting portion and a groove machined on an outer wall of a side of the bristle holder to keep a restriction pin being inserted in the groove, and the other end of the restriction pin being fixed onto a top wall of a pot-shaped mounting portion of a hollow support tube. When the brush head of the electric toothbrush having the above structure is in mass production, the restriction pin fixed in the hollow support tube may become loosened due to the error in the production process, thereby the restriction pin fails to fix the bristle holder reliably, causing the bristle holder disengaging from the hollow support tube. If the user has used the brush head of the electric toothbrush for an extended period of time, the groove of the bristle holder and the restriction pin are seriously wear, or the fixation between the restriction pin and the hollow support tube become loosened, resulting in the bristle holder disengaging from the hollow support tube. Some serious consequences will follow, for example, the user may swallow the bristle holder into his/her trachea, stomach, etc., if the bristle holder disengages from the hollow support tube during movement. What's even worse, the bristle holder may be stuck in the throat such that the user may have problem in breathing.

Several types of brush heads of the electric toothbrush on the market have been recalled for many times since the user is injured by the disengagement of the bristle holder from the product. Another patent application (publication No. CN 103784207A) of the inventor of the invention discloses a personal electric cleaning tool having a head connected with a carrier that carries cleaning element. The carrier includes a connecting part that can be accommodated within the head and a securing part for securing the cleaning element. The securing part extends from the connecting part along its first rotational axis and simultaneously extends in the radial direction perpendicular to the first rotational axis. The connecting part is provided with a pair of opposite arc-shaped grooves circumferentially on its external surface. Correspondingly, the head is provided with a pair of opposite stop pins in radial direction, wherein one end of each of the stop pins is fixed onto the head, while the other end protrudes to the interior of the head so as to be accommodated and engaged with the arc-shaped grooves respectively. Thereby, when the carrier rotates around the first rotational axis, the stop pins are positioned within and engaged with the corresponding arc-shaped grooves all the time, such that the disengaging of the carrier from the head is limited.

SUMMARY

The object of the present invention is to provide a reciprocally rotatable brush head which has a safe structure capable of preventing the carrier from disengaging from the head and different from that in prior art. Furthermore, the brush head is compact, simple in structure and easy to assemble.

To this end, the present invention provides a reciprocally rotatable brush head comprising: an interface (or port) of the brush head detachably connected with a handle, a housing of the brush head, a driving shaft of the brush head, a coupling of the brush head that couples a driving shaft of the handle with the driving shaft of the brush head, at least one brush disc, a cleaning element distributed on the brush disc, and a driving wheel tightly coupled with the driving shaft of the brush head; wherein the housing of the brush head is provided with a top hole and/or a central through hole which are/is centrally distributed, the rotation axis of the driving shaft of the brush head and the center line of the top hole and/or a central through hole are on the same straight line. The driving shaft of the brush head passes through the central through hole of the housing of the brush head. The driving shaft of the brush head may rotate freely within the top hole and/or the central through hole of the housing of the brush head in a reciprocal manner and is restrained within the housing of the brush head by the top hole and/or central through hole to rotate reciprocally around the rotation axis of the driving shaft of the brush head. The driving wheel is arranged with a through hole of the driving wheel through which a portion of the driving shaft of the brush head may pass. After the portion of the driving shaft of the brush head passing through the through hole of the driving wheel, a cooperation region of the driving shaft of the brush head with the driving wheel enters into the through hole of the driving wheel, the cooperation region having such a shape that the driving shaft of the brush head and the driving wheel are fixedly coupled together immovably. The brush disc is arranged with a protrusion of the brush disc toward a direction away from the cleaning element along a rotation axis of the brush disc. The protrusion of the brush disc is arranged with a driven portion of a driven wheel of the brush disc matching with a driving portion of the driving wheel and is provided with a hollow region of the brush disc along the direction of rotation axis of the driving shaft of the brush head. The driving shaft of the brush head passes through or enters into the hollow region of the brush disc and restricts the movement of the brush disc along the rotation axis of the brush disc toward the direction of the cleaning element. When the driving shaft of the brush head is not installed or is damaged, the brush disc does not perform reciprocating rotary movement. The top hole may be a blind hole, or a through hole.

Preferably, a driving portion of the driving wheel is arranged on the driving wheel, which is located at a side away from the cleaning element with respect to the rotation axis of the driving shaft of the brush head that is a centerline. The rotation axis of the driving shaft of the brush head and the rotation axis of the brush disc are substantially perpendicular to each other, such that the driven portion of the driven wheel of the brush disc is properly fitted to the driving portion of the driving wheel by passing across the rotation axis of the driving shaft of the brush head along the rotation axis of the brush disc in a direction from the cleaning element toward the driving wheel from a position away from the driving wheel.

The driving portion of the driving wheel may be a single conical tooth of a bevel gear which is arranged along the rotation axis of the brush disc in a direction away from the cleaning element. The driven portion of the driven wheel of the brush disc matching with the driving portion of the driving wheel is arranged on the protrusion of the brush disc toward a direction away from the cleaning element. The driven portion of the driven wheel of the brush disc is a single tooth groove structure that matches the single conical tooth on the driving wheel, the single tooth groove structure is formed by two opposite tooth form faces of the same bevel gear.

Preferably, a portion of the driving shaft of brush head contained in the hollow region of the brush disc has a length upward along the rotation axis of the driving shaft of the brush head greater than a distance by which the driving wheel disengages from the driven portion of the driven wheel of the brush disc. Preferably, the driving shaft of the brush head is made of metal.

A head of the housing of the brush head further includes a recess region that restricts a movement of the protrusion of the brush disc in a direction perpendicular to the rotation axis of the brush disc, that is, the housing of the brush head restricts a movement of the brush disc in the direction perpendicular to the rotation axis of the brush disc.

The driving portion of the driving wheel on the driving wheel may be designed to be generally sphere or cylinder, and the driven portion of the driven wheel of the brush disc is provided with two facets parallel with each other in a direction substantially perpendicular to the rotation axis of the driving shaft of the brush head. There is a movement gap between the two facets parallel with each other and the driving portion of the driving wheel, and the parallel faces of the two facets parallel with each other are tangential to the driving portion of the driving wheel.

The protrusion of the brush disc is arranged with a rotary surface of the brush disc, and a side of the recess region of the head of the housing of the brush head is arranged with an inner surface of the housing of the brush head. The rotary surface of the brush disc may be an entire or part of a cylindrical lateral surface when the rotation axis of the brush disc is its longitudinal axis, or an entire or part of a conical lateral surface when the rotation axis of the brush disc is its longitudinal axis. The inner surface of the housing of the brush head may be an entire or part of a cylindrical lateral surface when the rotation axis of the brush disc is its longitudinal axis, or an entire or part of a conical lateral surface when the brush disc rotation axis is its longitudinal axis.

The brush head may further comprise two brush discs, that is, a first brush disc and a second brush disc. The first and second brush discs may have same or opposite rotation directions, the first brush disc and the second brush disc each comprise protrusions of the brush disc. These protrusions of the brush disc are arranged with driven portions of the driven wheel of the brush disc matching with the corresponding driving portions of the driving wheel and the hollow regions of the brush disc in the direction of the rotation axis of the driving shaft of the brush head. The driving shaft of the brush head having the two brush discs passes through or enters into the hollow region of the brush discs of the first and second brush discs, and is restrained in the housing of the brush head of the brush head having two brush discs by a top hole and/or central through hole of the housing of the brush head so as to rotate reciprocally around the rotation axis of the driving shaft of the brush head.

According to the present invention, the top hole and/or the central through hole of the housing of the brush head limits the driving shaft of the brush head to merely rotating around the rotation axis of the driving shaft of the brush head, while restricts the movement of the driving shaft of the brush head along the direction of the rotation axis of the brush disc. The lower wall of the hollow region of the brush disc together with the driving shaft of the brush head restrained within the housing of the brush head effect collectively and may restrict the movement of the brush disc along the rotation axis of the brush disc toward the direction of the cleaning element. Thus, any personal injury caused by the disengaging of the brush disc from the housing of the brush head while reciprocally rotating around the rotation axis of the brush disc is prevented effectively.

Furthermore, according to the structure of the present invention, it is possible to first fix the driving wheel by fixture, and then the driven portion of the driven wheel of the brush disc is fitted to a position where it is properly engaged with the driving wheel by passing across the driving wheel. The assembly operation is simple and reliable, and thus the production efficiency is greatly improved.

Figure 1:
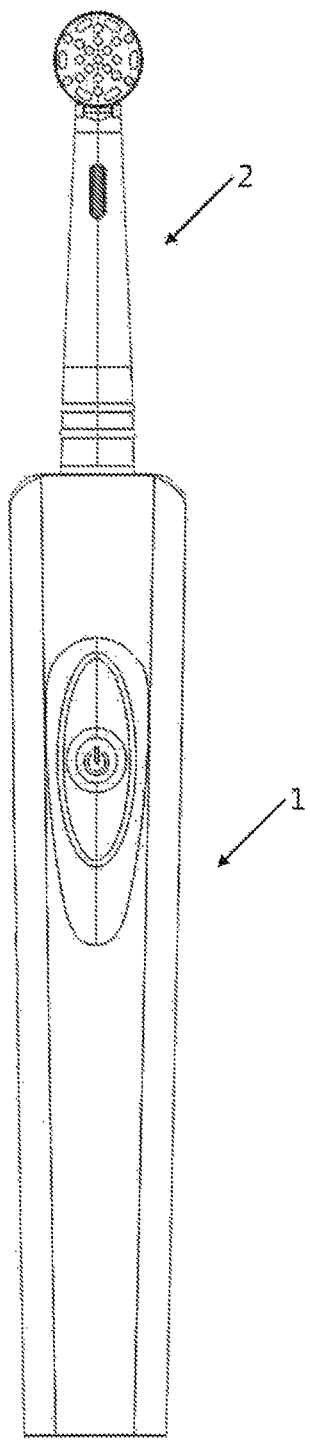
FIG. 1 is a front view of the electric toothbrush of the present invention.
Figure 2:
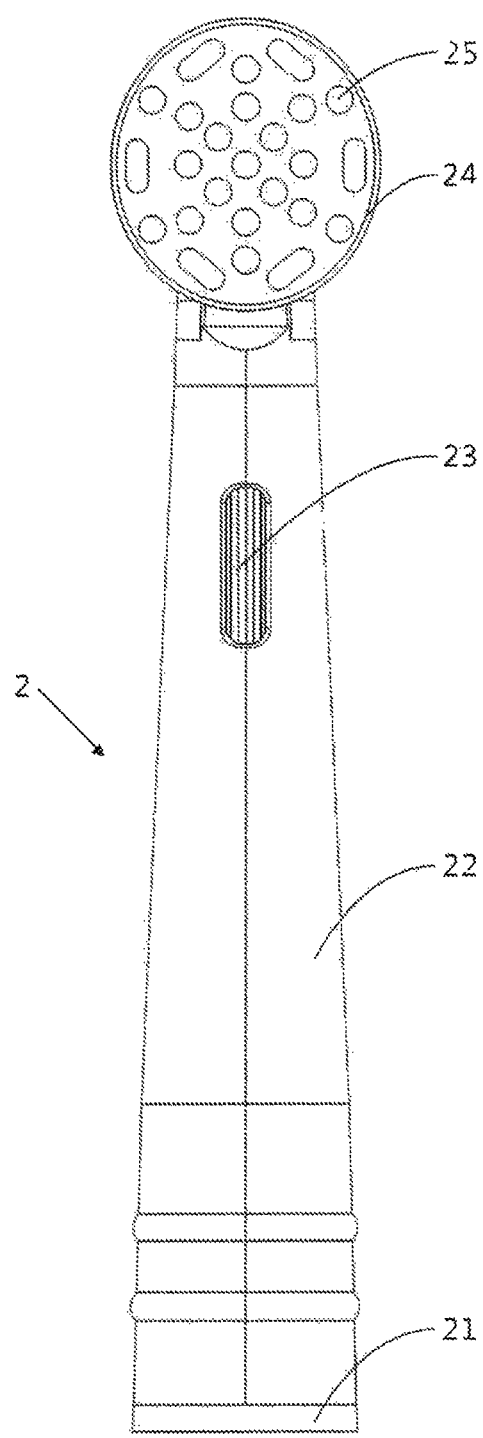
FIG. 2 is a front view of the brush head of the electric toothbrush as shown in FIG. 1.

DESCRIPTION OF MAIN REFERENCE NUMERALS 1 handle of the electric toothbrush
2 brush head 11 driving shaft of the handle
21 interface of the brush head
22 housing of the brush head
23 coupling of the brush head
24 brush disc
25 cleaning element
26 driving shaft of the brush head
27 driving wheel
34 brush disc of the second embodiment
36A driving shaft of the brush head of the driving wheel having a spherical driving portion in the second embodiment
36B driving shaft of the brush head of the driving wheel having a cylindrical driving portion in the second embodiment
37A driving wheel having a spherical driving portion in the second embodiment
37B driving wheel having a cylindrical driving portion in the second embodiment
50 brush head having two brush discs in the third embodiment
52 housing of the brush head of the brush head having two brush discs in the third embodiment
54A first brush disc of the third embodiment
54B second brush disc of the third embodiment
55A first cleaning element of the third embodiment
55B second cleaning element of the third embodiment
56 driving shaft of the brush head having two brush discs in the third embodiment
57 driving wheel of the brush head having two brush discs in the third embodiment
221 top hole of the housing of the brush head
222 inner surface of the housing of the brush head
223 central through hole of the housing of the brush head
224 recess region of the head of the housing of the brush head
$L_1$ rotation axis of the driving shaft of the brush head
$L2$ rotation axis of the brush disc
241 hollow region of the brush disc
242 rotary surface of the brush disc
243 driven portion of a driven wheel of the brush disc
244 lower wall of the hollow region of the brush disc
245 protrusion of the brush disc
261 top end of the driving shaft of the brush head
262 cooperation region of the driving shaft of the brush head with the coupling of the brush head
263 cooperation region of the driving shaft of the brush head with the driving wheel
271 driving portion of the driving wheel
272 through hole of the driving wheel
341 hollow region of the brush disc of the second embodiment
342 rotary surface of the brush disc of the second embodiment
343 driven portion of the driven wheel of the brush disc that cooperates with the cylindrical driving portion of the driving wheel in the second embodiment
344 lower wall of the hollow region of the brush disc of the second embodiment
345 protrusion of the brush disc of the second embodiment
371A spherical driving portion of the driving wheel of the second embodiment
371B cylindrical driving portion of the driving wheel of the second embodiment
372A, 372B through hole of the driving wheel of the second embodiment
521 top hole of the housing of the brush head of the third embodiment
523 central through hole of the housing of the brush head of the third embodiment
541A hollow region of the first brush disc of the third embodiment
541B hollow region of the second brush disc of the third embodiment
544A lower wall of the hollow region of the first brush disc of the third embodiment
544B lower wall of the hollow region of the second brush disc of the third embodiment
561 top end of the driving shaft of the brush head of the third embodiment
571 first driving portion of the driving wheel of the third embodiment
572 second driving portion of the driving wheel of the third embodiment

DETAILED DESCRIPTION

Hereafter, a description will be made to the exemplary embodiment of the present invention in more detail with a brush head of an electric toothbrush as an example in conjunction with the drawings. Although the illustration hereinafter is made merely in view of an electric toothbrush, the present invention is not limited thereto. Apparently, the present invention is also applied to other reciprocally rotatable brush head(s).

In the present invention, the terms indicating spatial relative positions, such as "inside", "outside", "up", "down", "upper" (or upper end), "lower" (or lower end), etc., are used to briefly describe the relationship of one element or feature relative to another element(s) or feature(s) as shown in the drawings. In this description, the terms "inside" and "outside" are defined with respect to the radial direction of the electric toothbrush, where being adjacent to its center is defined as "inside", and being away from its center is defined as "outside"; the terms "up", "down", "upper", "lower", "upper end", "lower end" are defined with respect to the longitudinal axis of the electric toothbrush, where the end adjacent to the brush disc is defined as "up", "upper" or "upper end", and the end opposite thereto is defined as "down", "lower", or "lower end", when the electric toothbrush works at an upright or inclined state.

When an element is described as "placed onto . . . " or "coupled to . . . " another element, it may be either directly located on or coupled to another element, or there may be intervening element(s) located between the element and the other element. However, when an element is described as "directly placed onto . . . " or "directly coupled to . . . " another element, there is no intervening element(s) located between the element and the other element. As to other wordings and expressions describing the relationship among elements, it will be appreciated that the similar meanings (e.g., "between . . . " and correspondingly "directly between . . . ", and the like) is embraced.

Although the terms "first", "second", etc., are used in the present invention to describe a plurality of elements or constituents, these elements or constituents should not to be limited by these words. These words are used simply to distinguish one element or constituent from another element or constituent, without including any "order". Thus, the first element or constituent discussed below referred to as a second element or constituent does not go beyond the concept and scope of the present invention.

Referring to FIGS. 1 to 4, the electric toothbrush in an embodiment of the present invention includes a handle 1 accommodating a driving portion therein and a brush head 2 detachably coupled to the handle 1. The brush head 2 includes an interface of the brush head 21, a housing of the brush head 22, a coupling of the brush head 23, a brush disc 24, a cleaning element 25, a driving shaft of the brush head 26, and a driving wheel 27. The brush head 2 is detachably mounted to the handle 1 through the interface of the brush head 21. The driving shaft of the handle 11 may rotate around the rotation axis $L_1$ of the driving shaft of the brush head reciprocally.

Figure 3:
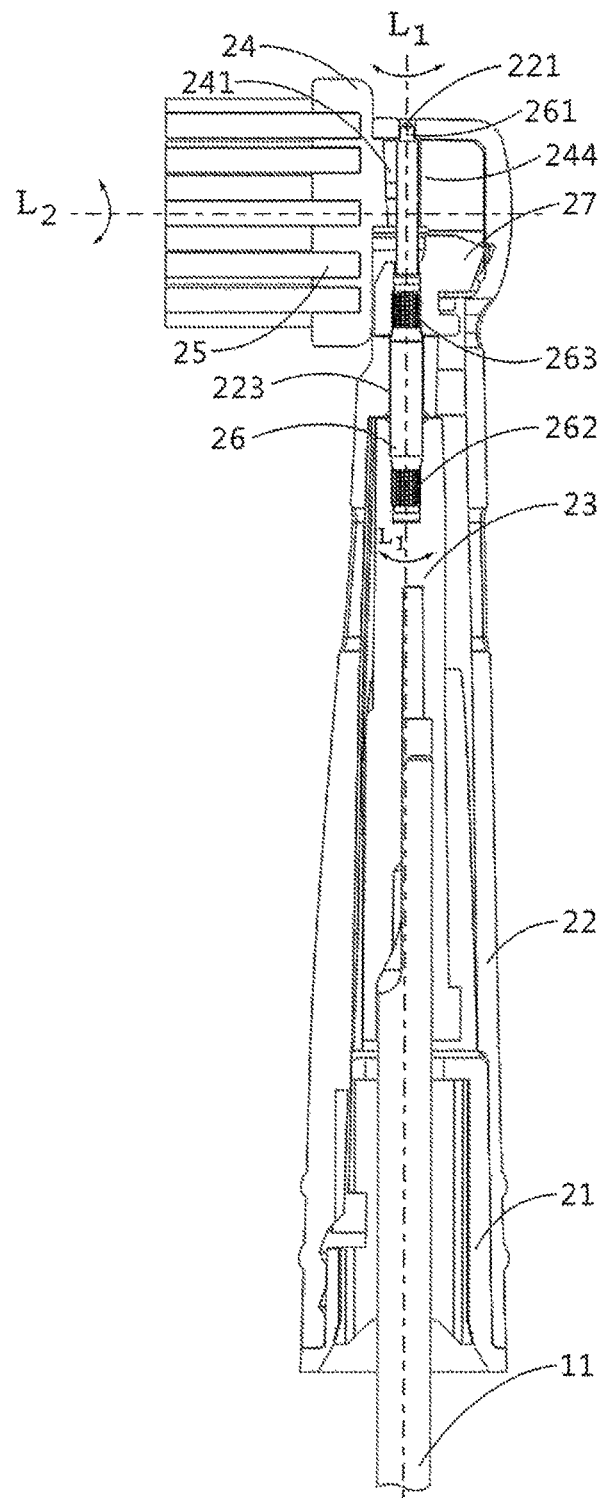
FIG. 3 is a side sectional view of the brush head of the electric toothbrush as shown in FIG. 2.
Figure 4:
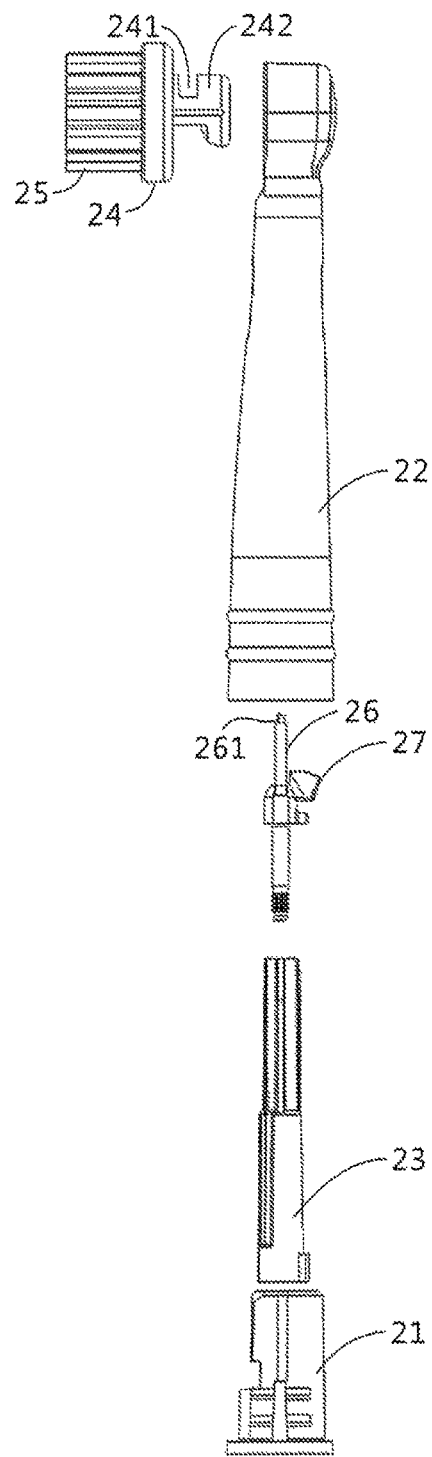
FIG. 4 is an exploded schematic view of the brush head of the electric toothbrush as shown in FIG. 2.

As shown in FIG. 3, the driving shaft of the handle 11 is inserted into the lower end of the coupling of the brush head 23. As well known to the skilled in the art, once the shape of the cooperation region of the driving shaft of the handle 11 with the coupling of the brush head 23 (for example, tight fit by facets) is properly designed, the coupling of the brush head 23 may be driven to reciprocally rotate around the rotation axis $L_1$ of the driving shaft of the brush head as the driving shaft of the handle 11 rotates. The driving shaft of the brush head 26 is tightly inserted into the upper end of the coupling of the brush head 23. Once the shape of the cooperation region of the driving shaft of the brush head 26 with the coupling of the brush head 23 is properly designed (for example, local knurling process is used to the driving shaft of the brush head 26, as shown at 262 in FIG. 5), the driving shaft of the brush head 26 may be immovably coupled to the coupling of the brush head 23, and the driving shaft of the brush head 26 and the coupling of the brush head 23 have the same reciprocal rotation axis, i.e., the rotation axis $L_1$ of the driving shaft of the brush head. That is, both the driving shaft of the brush head 26 and the coupling of the brush head 23 rotate around the rotation axis $L_1$ of the driving shaft of the brush head reciprocally.

Figure 5:
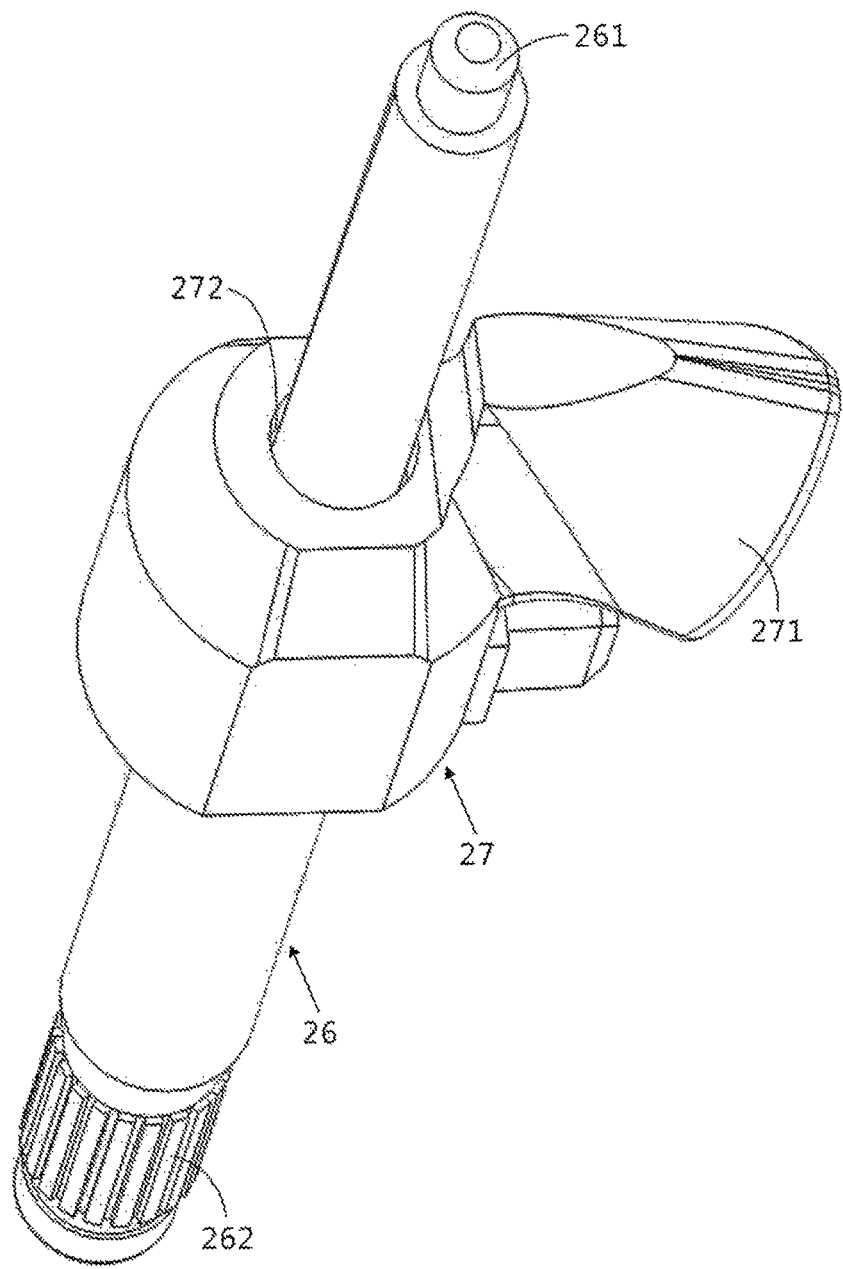
FIG. 5 is an assembly view of the driving shaft of the brush head and the driving wheel as shown in FIG. 2.
Figure 6:
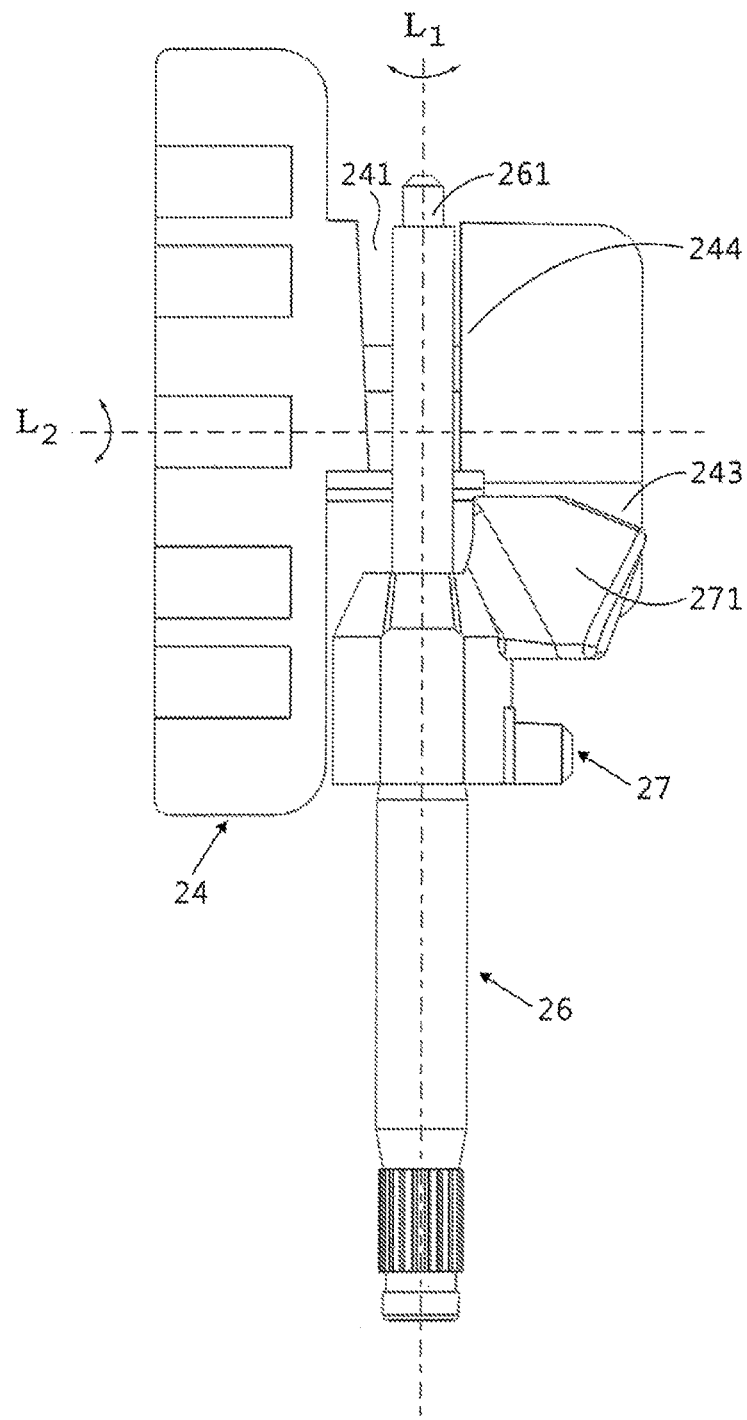
FIG. 6 is an assembly sectional view of the driving shaft of the brush head, driving wheel and brush disc as shown in FIG. 2.
Figure 7:
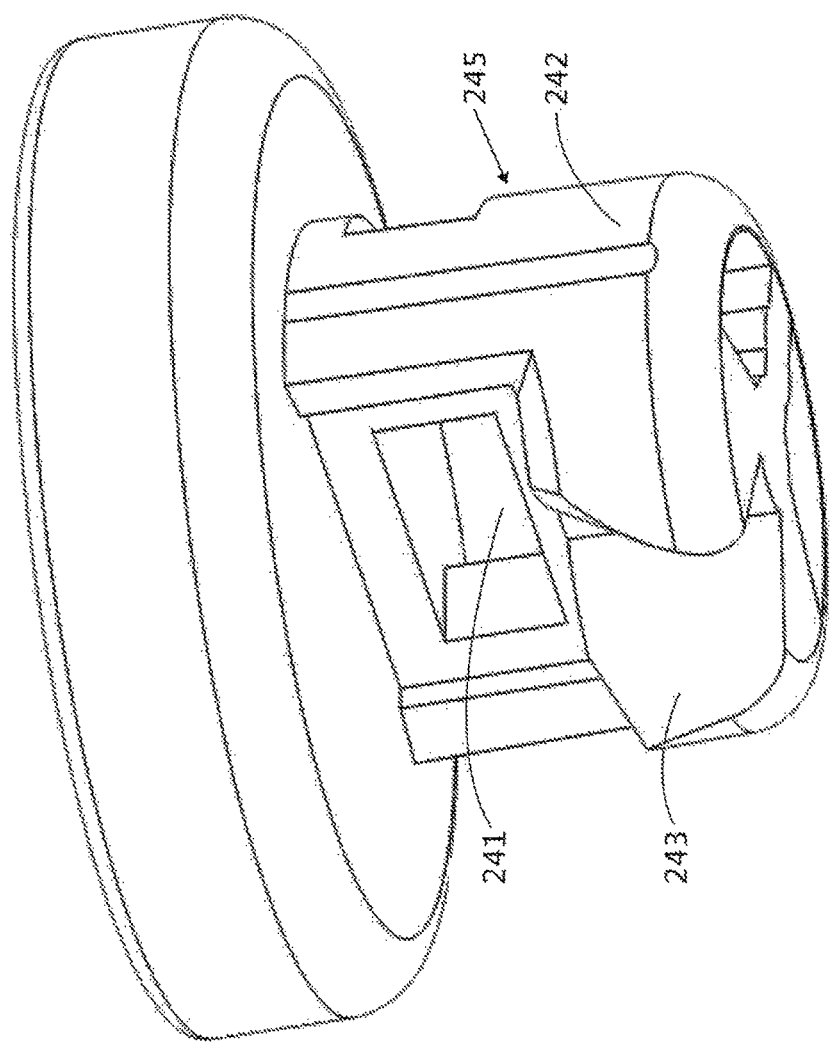
FIG. 7 is a perspective view of the brush disc of the toothbrush as shown in FIG. 1.

The driving shaft of the brush head 26 passes through the central through hole 223 of the housing of the brush head and rotates freely within the central through hole 223 of the housing of the brush head in a reciprocal manner, which is a movable shaft-hole fit that is typically used in engineering. The driving shaft of the brush head 26 is firmly coupled with the driving wheel 27 above the central through hole 223 of the housing of the brush head. As shown in FIG. 5, the driving wheel 27 is arranged with a through hole 272 of the driving wheel, and a portion of the driving shaft of the brush head 26 may pass through the through hole of the driving wheel 272. After the portion of the driving shaft of the brush head 26 passes through the through hole of the driving wheel 272, the cooperation region 263 of the driving shaft of the brush head with the driving wheel enters into the through hole of the driving wheel 272, and the cooperation region 263 of the driving shaft of the brush head with the driving wheel has such a shape that the driving shaft of the brush head 26 and the driving wheel 27 are immovably coupled together without any relative movement therebetween. As shown in FIG. 3, the driving shaft of the brush head 26 passes through the hollow region of the brush disc 241 above the driving wheel 27, and the brush disc 24 may freely rotate around the rotation axis $L_2$ of the brush disc in a reciprocal manner according to a predetermined angle without interference from the driving shaft of the brush head 26. The rotation axis $L_1$ of the driving shaft of the brush head and the rotation axis $L_2$ of the brush disc are substantially perpendicular to each other. The top end 261 of the driving shaft of the brush head is inserted into the top hole 221 of the housing of the brush head above the hollow region of the brush disc 241 and may rotate freely about the rotation axis $L_1$ of the driving shaft of the brush head in a reciprocal manner with respect to the top hole 221 of the housing of the brush head. The top hole 221 of the housing of the brush head and the central through hole 223 of the housing of the brush head are centrally distributed, that is, the center lines of the two holes are on the same straight line, and the rotation axis $L_1$ of the driving shaft of the brush head and the center lines of the two holes are on the same straight line. The driving shaft of the brush head 26 of the present invention is made of metal, and certainly, the driving shaft of the brush head 26 may also be made of plastic. Due to higher elastic modulus of the metal as compared with the plastic, the metallic part has better geometry dimensional accuracy and movement stability than the plastic part.

As shown in FIGS. 4, 7, 8 and 10, a cleaning element 25 is distributed on the brush disc 24. The brush disc 24 is arranged with a protrusion of the brush disc 245 in a direction of the rotation axis $L_2$ of the brush disc away from the cleaning element 25, and the protrusion of the brush disc 245 is provided with a hollow region of the brush disc 241 in the direction of the rotation axis $L_1$ of the driving shaft of the brush head. The driving shaft of the brush head 26 passes through the hollow region of the brush disc 241. When the brush disc 24 reciprocally rotates around the rotation axis $L_2$ of the brush disc, the hollow region of the brush disc 241 prevents any movement interference between the brush disc 24 and the driving shaft of the brush head 26. The protrusion of the brush disc 245 is arranged with a driven portion 243 of the driven wheel of the brush disc matching with the driving wheel 27. In this embodiment, the driving portion 271 of the driving wheel 27 includes a single conical tooth of a bevel gear, and the single conical tooth is arranged along the rotation axis of the brush disc $L_2$ in a direction away from the cleaning element 25, that is, the driving portion 271 (the single conical tooth) of the driving wheel is located at a side away from the cleaning element 25 when the rotation axis $L_1$ of the driver shaft of the brush head is the centerline. The driven portion 243 of the driven wheel of the brush disc which matches with the driving portion 271 of the driving wheel is arranged on the protrusion of the brush disc 245 toward a direction away from the cleaning element 25. In this embodiment, the driven portion 243 of the driven wheel of the brush disc has a single tooth groove structure that matches with the single conical tooth of the driving portion 271 of the driving wheel 27 and is formed by two opposite tooth form faces on the same bevel gear.

The housing of the brush head 22 is arranged with a recess region 224 of a head of the housing of the brush head in the head region, and the protrusion of the brush disc 245 is accommodated by the recess region 224 of the head of the housing of the brush head. The protrusion of the brush disc 245 is arranged with a rotary surface of the brush disc 242. An inner surface 222 of the housing of the brush head is arranged on the side of the recess region 224 of the head of the housing of the brush head. In this embodiment, the rotary surface of the brush disc 242 may be an entire or part of a cylindrical lateral surface when taking the rotation axis $L_2$ of the brush disc as its longitudinal axis, or an entire or part of a conical lateral surface when taking the rotation axis $L_2$ of the brush disc as its longitudinal axis. The inner surface 222 of the housing of the brush head may be an entire or part of a cylindrical lateral surface when taking the rotation axis $L_2$ of the brush disc as its longitudinal axis, or an entire or part of a conical lateral surface when taking the rotation axis $L_2$ of the brush disc as its longitudinal axis. There is a movement gap between the rotary surface 242 of the brush disc and the inner surface 222 of the housing of the brush head, and the movement gap allows the protrusion of the brush disc 245 to rotate freely around the rotation axis $L_2$ of the brush disc in the recess region 224 of the head of the housing of the brush head in a reciprocal manner. The rotary surface of the brush disc 242 and the inner surface 222 of the housing of the brush head cooperate so as to restrain the brush disc 24 to rotate about the rotation axis $L_2$ of the brush disc reciprocally.

Figure 8:
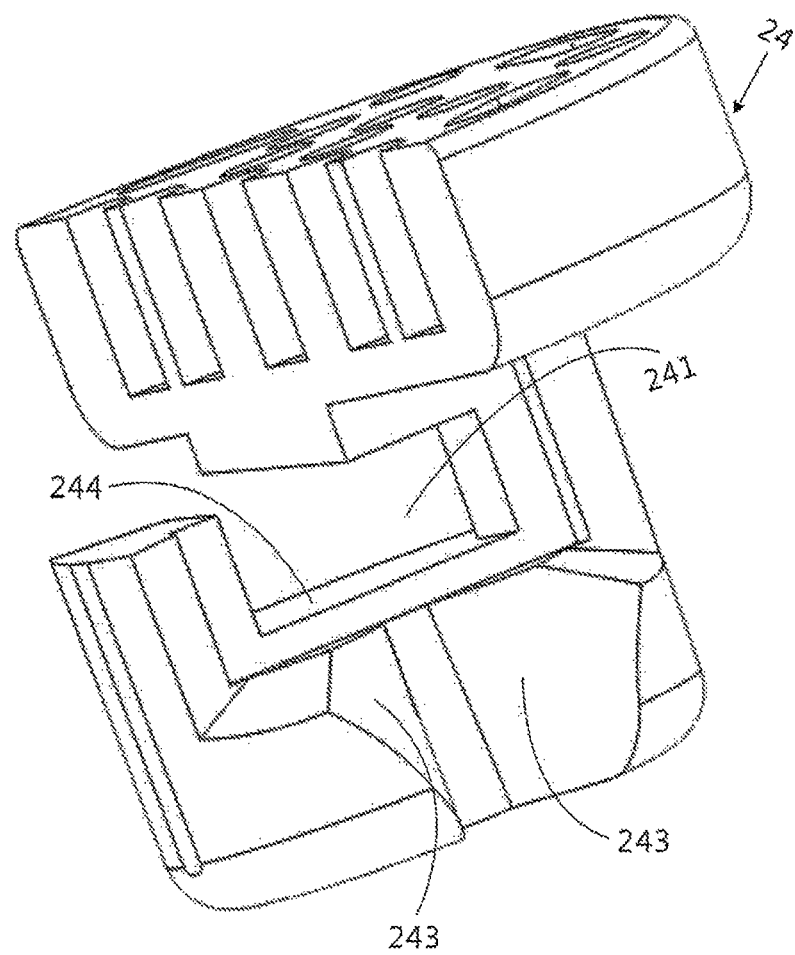
FIG. 8 is a partial sectional view of FIG. 7.
Figure 9:
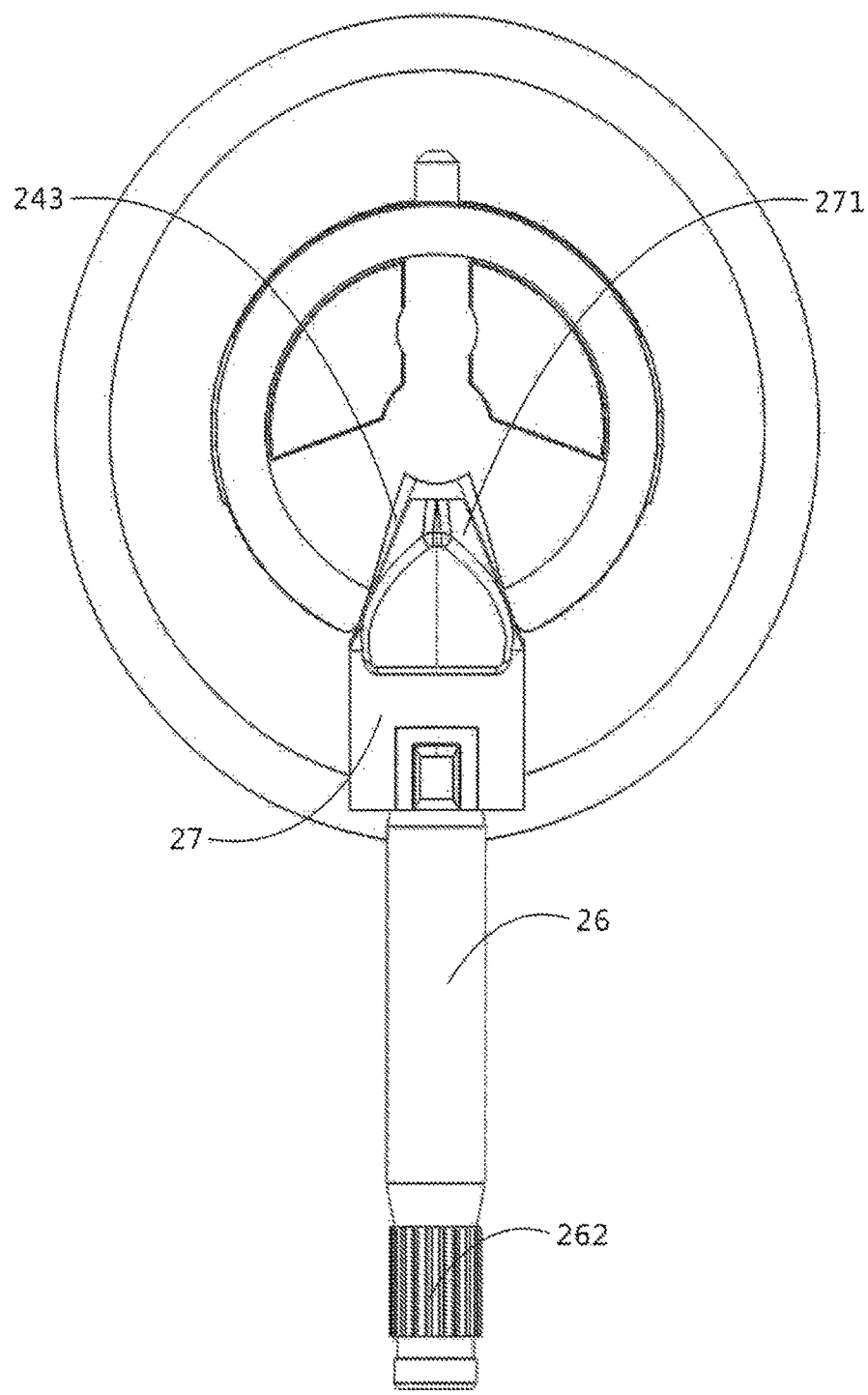
FIG. 9 is an assembly front view of the driving shaft of the brush head, driving wheel and brush disc as shown in FIG. 2.
Figure 10:
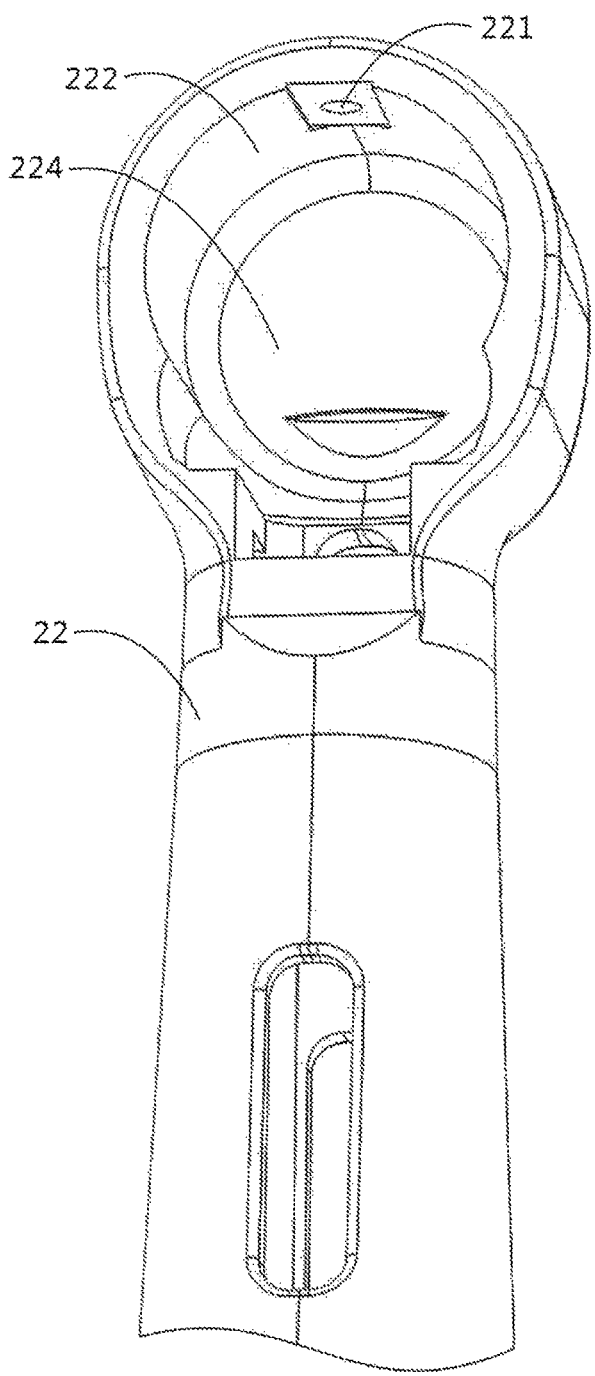
FIG. 10 is a partial sectional view of the housing of the brush head as shown in FIG. 2.
Figure 11:
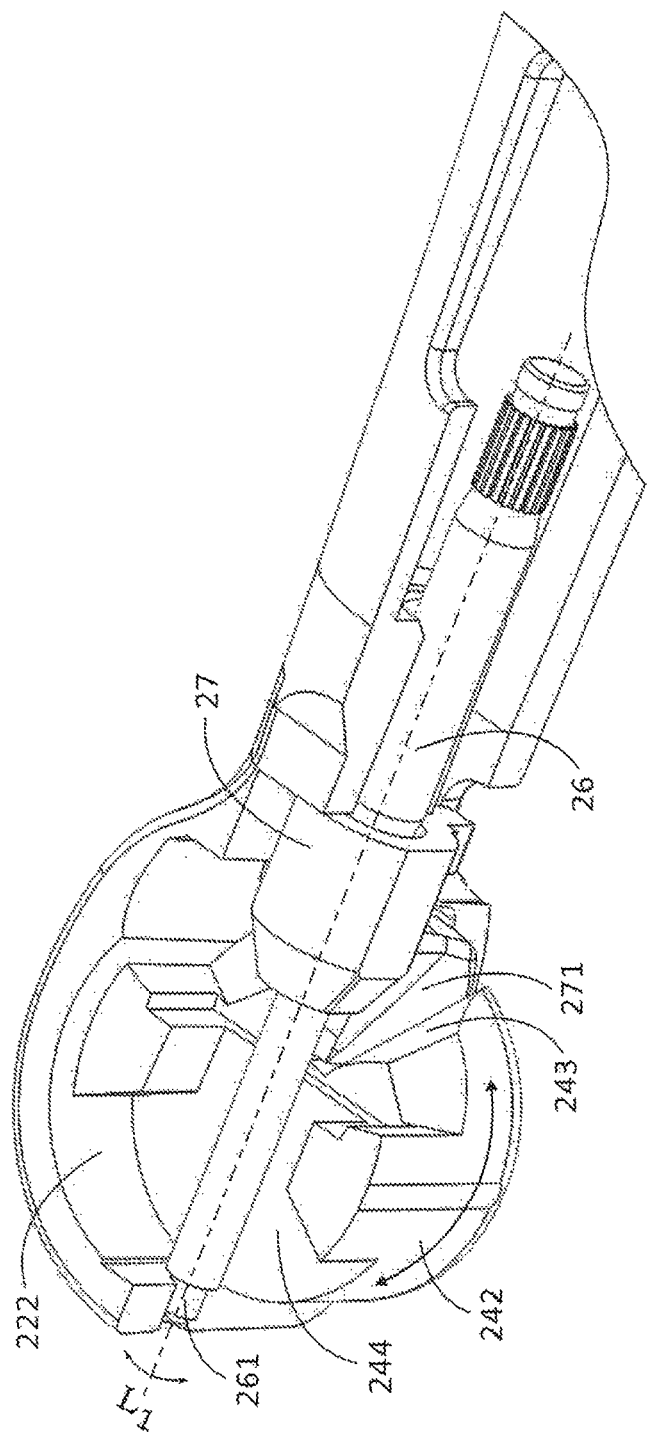
FIG. 11 is a partial sectional view of the assembly of the housing of the brush head, brush disc, driving shaft of the brush head and driving wheel as shown in FIG. 2.

In the present invention, the transmission portion of the head includes a driving portion 271 of the driving wheel in a form of a single tooth of the bevel gear and a driven portion 243 of the driven wheel of the brush disc matching with the single tooth, and the driven portion 243 is in a form of a single tooth groove structure being formed by two opposite tooth form faces of the same bevel gear. As shown in FIGS. 9 and 3, due to the fact that the driving portion 271 of the driving wheel is a single conical tooth of a bevel gear and the housing of the brush head 22 is arranged with a recess region 224 of the head of the housing of the brush head (FIG. 10) for accommodating the protrusion of the brush disc 245, the driven portion 243 of the driven wheel of the brush disc may be assembled to a region provided with the driving portion 271 of the driving wheel by passing across the rotation axis of the driving wheel 27 along the rotation axis $L_2$ of the brush disc from the side opposite to the side where the single conical tooth is arranged with regard to the rotation axis of the driving wheel 27 which is centerline, such that the driven portion 243 of the driven wheel of the brush disc and the driving portion 271 of the driving wheel are properly engaged, when the driving shaft of the brush head 26 is not yet inserted into the driving wheel 27 and the driving portion 271 of the driving wheel is located at the side away from the cleaning element 25 with regard to the the rotation axis $L_1$ of the driving shaft of the brush head which is centerline. Therefore, the brush disc 24 and the driving wheel 27 can be assembled more flexibly. Otherwise, the driving wheel 27 has to be mounted into the driven portion 243 of the driven wheel of the brush disc in advance, and then the assembly is placed into the recess region 224 of the head of the housing of the brush head. Apparently, the accurate engagement state between the driving wheel 27 and the driven portion 243 of the driven wheel of the brush disc could hardly be ensured by this method. According to the structure of the present example, it is possible to first fix the driving wheel 27 by fixture, and then assembly the driven portion 243 of the driven wheel of the brush disc to the position that properly engaged with the driving wheel 27 by passing across the driving wheel 27. The assembly operation is simple and reliable, and the production efficiency has been greatly improved. FIG. 8 is a partial sectional view of the brush disc 24, showing clearly the hollow region of the brush disc 241 and a lower wall 244 of the hollow region of the brush disc being provided in the direction of the hollow region of the brush disc 241 away from the cleaning element 25. FIG. 11 is a partial sectional view of the assembly of the brush disc 24, the housing of the brush head 22, the driving shaft of the brush head 26 and the driving wheel 27. As shown in FIG. 3, the central through hole 223 and the top hole 221 of the housing of the brush head restrain the driving shaft of the brush head 26 in such a way that it could simply rotate around the rotation axis $L_1$ of the driving shaft of the brush head, while restricting the movement of the driving shaft of the brush head 26 in the direction of the rotation axis $L_2$ of the brush disc. The top region of the hollow region of the brush disc 241 adjacent to the housing of the brush head is fan-shaped. When the driving wheel 27 is driven by the driving shaft 11 of the handle to rotates around the rotation axis $L_1$ of the driving shaft of the brush head reciprocally, the driving wheel 27 activates the driven portion 243 of the driven wheel of the brush disc, and the driven portion 243 of the driven wheel of the brush disc makes the brush disc 24 rotates around the rotation axis $L_2$ of the brush disc reciprocally. In this embodiment, the brush disc 24 is driven by the driving wheel 27 and has a unidirectional maximum rotation angle of about 60° around the rotation axis $L_2$ of the brush disc. Thus, the hollow region of the brush disc 241 is arranged to have a sufficiently large evacuation region to allow the brush disc 24 and the driving shaft of the brush head 26 to reciprocally rotate around the rotation axis $L_2$ of the brush disc without interference. Apparently, the larger the evacuation region of the hollow region 241 of the brush disc is, the better for the brush disc 24 and the driving shaft of the brush head 26 to reciprocally rotate around the rotation axis $L_2$ of the brush disc without interference. Since the evacuation region of this example is the hollow region of the brush disc 241, which means that the evacuation region should be surround by corresponding solid part(s). Furthermore, due to the fact that the driving shaft of the brush head 26 has a corresponding diameter, in industrial applications, it is required that the evacuation region 241 should be surrounded by solid part(s) with an appropriate wall thickness in consideration of the mechanical strength of the hollow region of the brush disc 241. Also, the evacuation region may not be oversized in consideration of the mechanical strength of the driving shaft of the brush head 26 that requires a proper diameter. The wall thickness of the solid part of the hollow region 241 and the diameter of the driving shaft 26 of the brush head restrict the angle at which the brush disc 24 rotates around the rotation axis $L_2$ of the brush disc and the driving shaft of the brush head 26 without interference. Tests shows that the evacuation region of the hollow region 241 of the brush disc may only allow a maximum unilateral rotation angle of about 150° of the reciprocal rotation of the brush disc 24 and the driving shaft of the brush head 26 about the rotation axis $L_2$ of the brush disc without interference. Preferably, the evacuation region of the hollow region 241 of the brush disc may allow a maximum unilateral rotation angle of 90° of the reciprocal rotation of the brush disc 24 and the driving shaft of the brush head 26 about the rotation axis $L_2$ of the brush disc without interference.

Also as shown in FIG. 3, the central through hole 223 and the top hole 221 of the housing of the brush head restrain the rotation of the driving shaft of the brush head 26 merely around the rotation axis $L_1$ of the driving shaft of the brush head, while restricting the movement of the driving shaft of the brush head 26 in the direction of the rotation axis $L_2$ of the brush disc. The hollow region of the brush disc 241 forms an annular entity that surrounds a portion of the driving shaft of the brush head 26 in the radial direction of the driving shaft of the brush head 26, and the driving shaft of the brush head 26 may pass through the hollow region of the brush disc 241 along the rotation axis $L_1$ of the driving shaft of the brush head freely. As above stated, the lower wall 244 of the hollow region of the brush disc cooperates with the driving shaft of the brush head 26 restrained within the housing of the brush head 22, such that the movement of the brush disc 24 toward the direction of the cleaning element 25 along the rotation axis $L_2$ of the brush disc is restricted, and thus any personal injury caused by the brush disc 24 disengaging from the housing of the brush head 22 when the brush disc 24 reciprocally rotates around the rotation axis L2 of the brush disc is effectively prevented. In the process of mass production, in the case that the finished product of brush head is not assembled with the driving shaft of the brush head 26, the driving wheel 27 may not move, and the brush disc 24 may not be driven by the driving wheel 27 either, such that the brush disc 24 is deprived of the function of moving, which can easily be recognized and picked out by the detection station of the production line. Similarly, if this happens when the product is being used, the user will immediately stop using and will not be injured even the brush head 2 is still being used due to the fact that the brush disc 24 can not move. Still further, according to common knowledge in mechanical field, if the driving wheel 27 moves toward the handle direction along the rotation axis $L_1$ of the driving shaft of the brush head by a distance disengaging the driving wheel 27 from the driven portion 243 of the driven wheel of the brush disc, the driving wheel 27 then will separate from the driven portion 243 of the driven wheel of the brush disc, that is, the driving wheel 27 may not drive the driven portion 243 of the driven wheel of the brush disc any more. In order to restrain brush disc 24 within the housing of the brush head 22 by the driving shaft of the brush head 26 more reliably during the movement, in this example, the driving shaft of the brush head 26 passes through or enters into the hollow region of the brush disc 241, and preferably the portion of the driving shaft of the brush head 26 surrounded by the hollow region of the brush disc 241 has an upward length along the rotation axis $L_1$ of the driving shaft of the brush head, and the upward length is greater than the distance disengaging the driving wheel 27 from the driven portion 243 of the driven wheel of the brush disc.

As stated above, the head of the housing of the brush head 22 is arranged with a recess region 224 of the head of the housing of the brush head which accommodates the protrusion of the brush disc 245. The protrusion of the brush disc 245 is restrained in the recess region 224 of the head of the housing of the brush head and rotates reciprocally around the rotation axis L2 of the brush disc. The recess region 224 of the head of the housing of the brush head restrains the protrusion of the brush disc 245 within the recess region 224 of the head of the housing of the brush head, i.e., the recess region 224 of the head of the housing of the brush head restricts the movement of the protrusion of the brush disc 245 in the direction perpendicular to the rotation axis L2 of the brush disc. That is, the housing of the brush head 22 restricts the movement of the brush disc 24 in the direction perpendicular to the rotation axis L2 of the brush disc.

When the user activates the handle 1 of the electric toothbrush to make the toothbrush work, the driving shaft 11 of the handle reciprocally rotates around the rotation axis $L_1$ of the driving shaft of the brush head and drives the coupling of the brush head 23, and the coupling of the brush head 23 drives the driving shaft of the brush head 26 and the driving wheel 27 to reciprocally rotate around the rotation axis $L_1$ of the driving shaft of the brush head. The driving wheel 27 drives the driven portion 243 of the driven wheel of the brush disc, so that the brush disc 24 reciprocally rotates around the rotation axis L2 of the brush disc and drives the cleaning element 25 (such as, bristles) fastened onto the brush disc 24 to reciprocally rotate to achieve the effect of cleaning teeth.

As stated above, the driving wheel 27 is mounted on the driving shaft of the brush head 26 and the driving wheel 27 is not movable relative to the drive shaft of the brush head 26. The driving portion 271 of the driving wheel is located at a side away from the cleaning element 25 with regard to the rotation axis $L_1$ of the brush head driving shaft which is centerline. The brush disc 24 is arranged with the protrusion of the brush disc 245 along the rotation axis L2 of the brush disc toward the direction away from the cleaning element 25, and the protrusion of the brush disc 245 is arranged with the driven portion 243 of the driven wheel of the brush disc that moves cooperatively with the driving wheel 27. The driving shaft of the brush head 26 drives the driving wheel 27 to move, and the driving wheel 27 drives the driven portion 243 of the driven wheel of the brush disc to move. The brush disc 24 moves and drives the cleaning element 25 to move, thus a cleaning effect is achieved. Apparently, a new drive assembly structure is obtained by rotating the driving wheel 27 and the driven portion 243 of the driven wheel of the brush disc around the rotation axis $L_1$ of the driving shaft of the brush head by 180°, which does not go beyond the scope of the present invention.

The driving shaft of the brush head 26 passes through or enters into the hollow region 241 of the brush disc, and is restrained in the housing of the brush head 22 by the top hole 221 and/or the central through hole 223 of the housing of the brush head 22 so as to rotate reciprocally around the rotation axis $L_1$ of the driving shaft of the brush head. The driving shaft of the brush head 26 restricts the movement of the brush disc 24 along the rotation axis $L_2$ of the brush disc toward the direction of the cleaning element 25, and the brush disc 24 of the brush head 2 fails to reciprocally rotate when the driving shaft of the brush head 26 is not installed or the driving shaft of the brush head 26 is damaged. The recess region 224 of the head of the housing of the brush head restricts the movement of the protrusion of the brush disc 245 in the direction perpendicular to the rotation axis of the brush disc $L_2$, that is, the housing of the brush head 22 restricts the movement of the brush disc 24 in the direction perpendicular to the rotation axis L2 of the brush disc, wherein the housing of the brush head 22 is a stationary part and the movable protrusion of the brush disc 245 is in the housing of the brush head 22 so that the human body's oral tissue may not make contact with the movable protrusion of the brush disc 245, which further ensures that the brush disc 24 does not harm the oral tissue during movement.

Figure 12A:
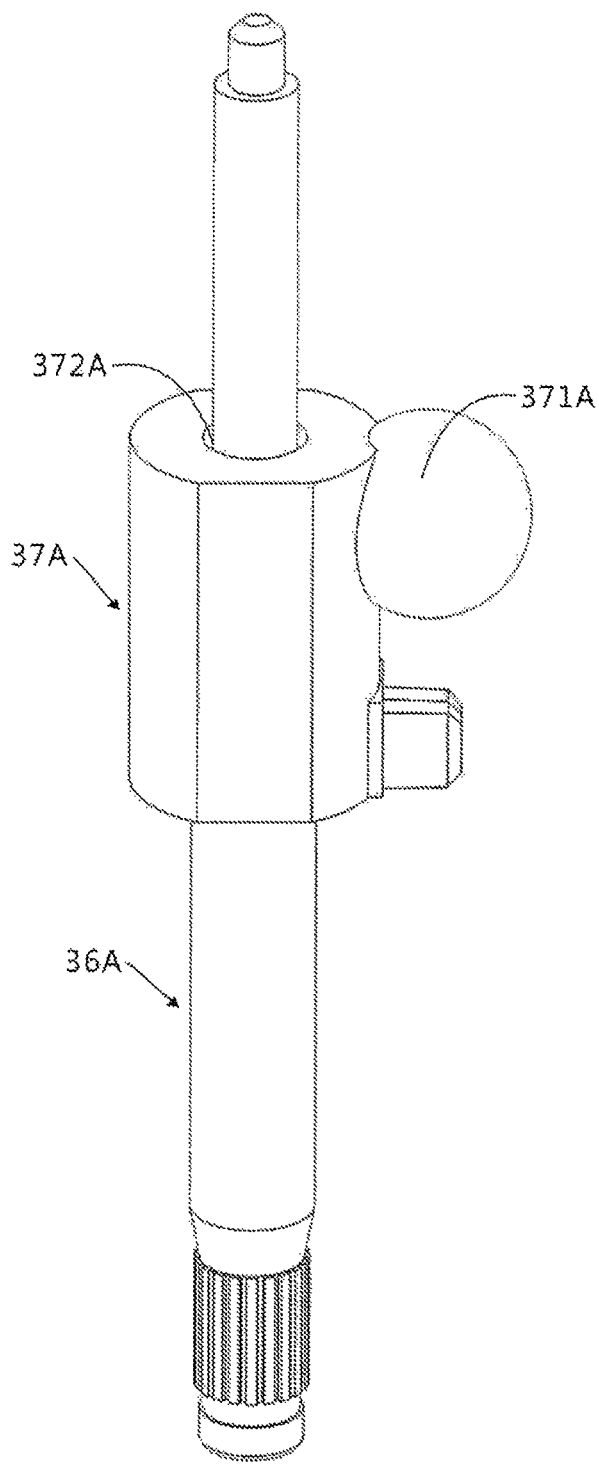
FIG. 12A is an assembly view of the driving shaft of the brush head and the driving wheel of the brush head of the electric toothbrush according to the second embodiment of the present invention, in which the driving portion of the driving wheel is a sphere.

Certainly, the driving portion 271 of the driving wheel is not limited to the single conical tooth structure of a bevel gear, and a driving wheel 37A of the second embodiment is shown in FIG. 12A. The driving wheel 37A is provided with a second driving portion 371A of the driving wheel which is an approximately sphere. The second driving wheel 37A is arranged with a second through hole 372A of the driving wheel in the direction of the rotation axis $L_1$ of the driving shaft of the brush head. The second through hole 372A of the driving wheel cooperates with the second driving shaft 36A so that the second driving wheel 37A is immovably fixed at an appropriate position of the second driving shaft 36A, so as to drive the second driven portion 343 of the driven wheel of the brush disc properly.

Figure 12B:
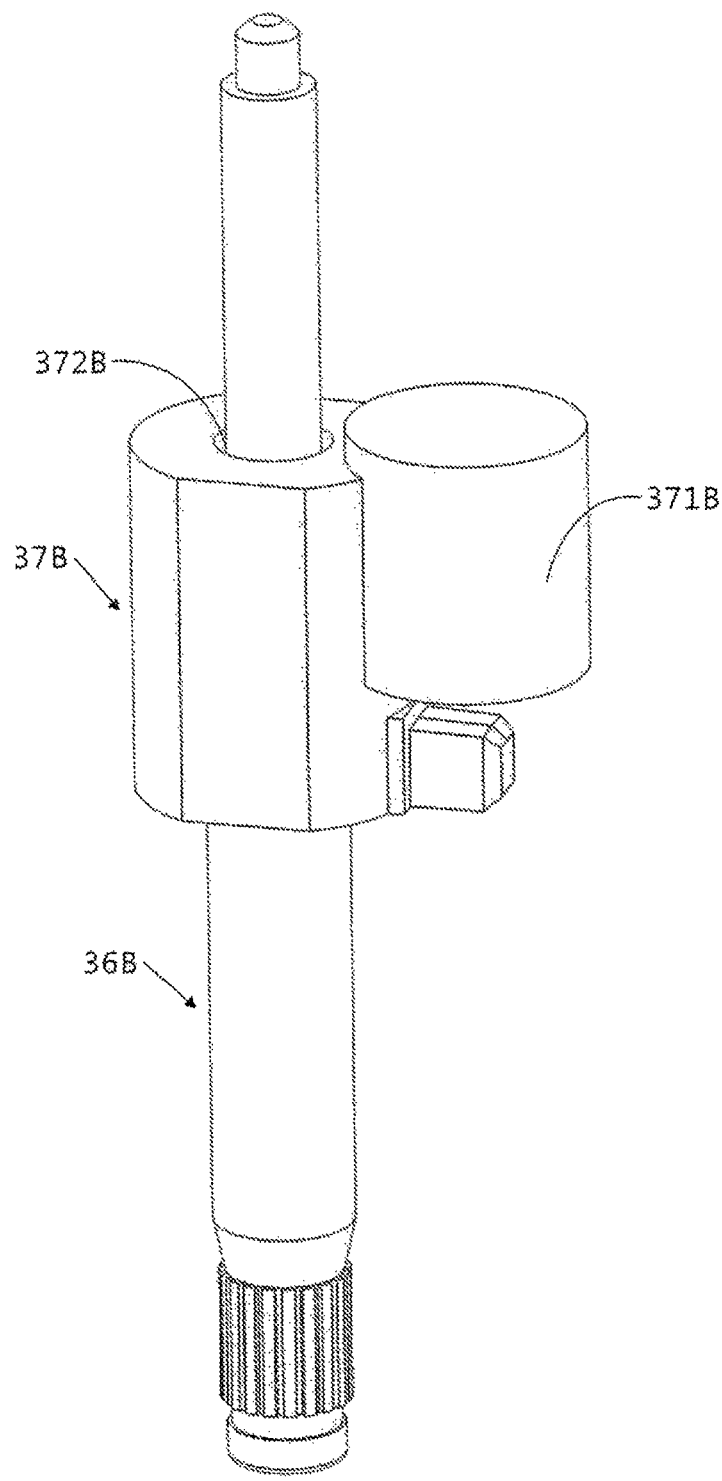
FIG. 12B is an assembly view of the driving shaft of the brush head and the driving wheel of the brush head of the electric toothbrush according to the second embodiment of the present invention, in which the driving portion of the driving wheel is a cylinder.
Figure 13:
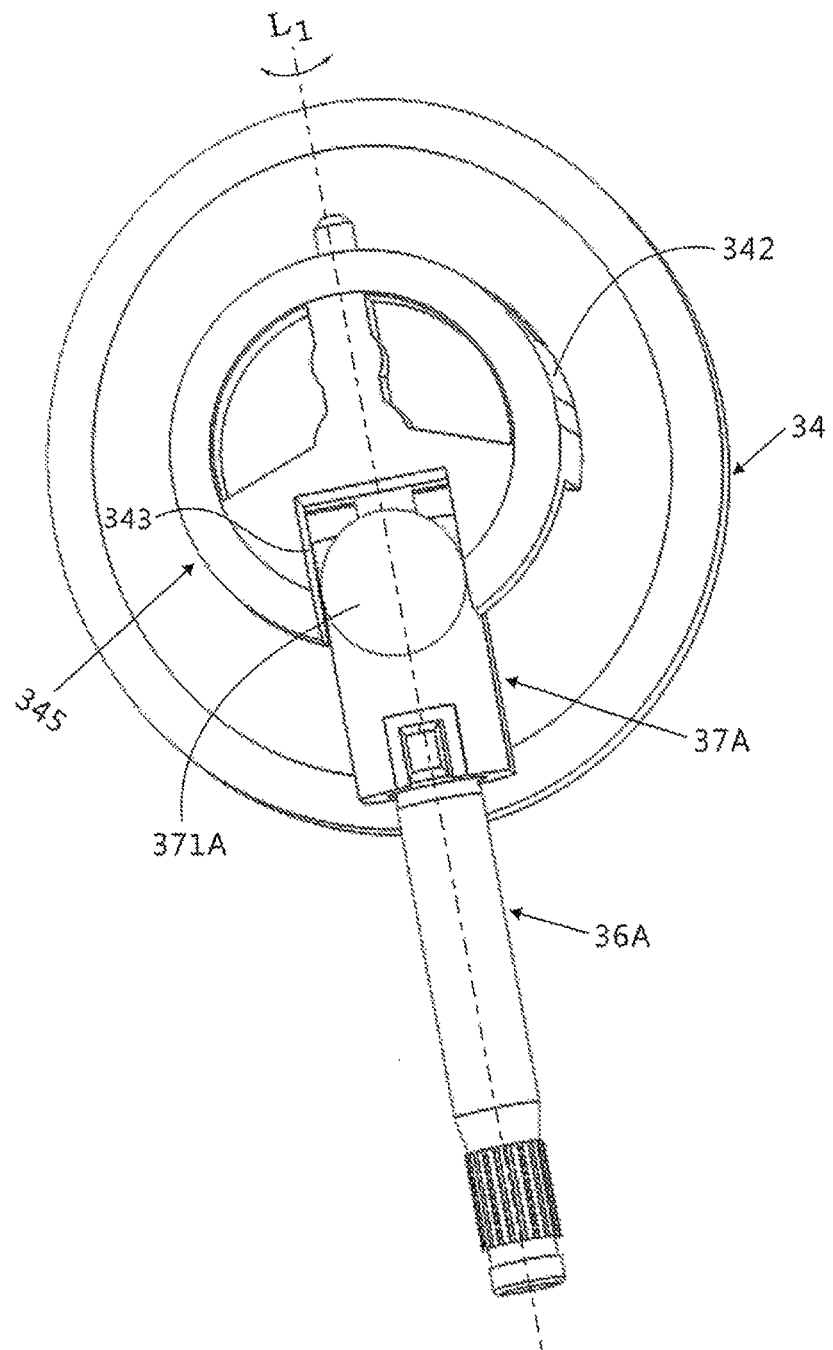
FIG. 13 is an assembly view of the driving wheel, the driving shaft of the brush head and the brush disc as shown in FIGS. 12A and 12B.

As shown in FIG. 13, the brush disc 34 of the second embodiment is arranged with a second protrusion of the brush disc 345 along the rotation axis L2 of the brush disc toward a direction away from the cleaning element 25. The second protrusion of the brush disc 345 is arranged with a second driven portion 343 of the driven wheel of the brush disc that matches the second driving portion 371A of the driving wheel in a direction away from the cleaning element 25. In this embodiment, as shown in FIG. 13, the second driven portion 343 of the driven wheel of the brush disc is arranged with two facets parallel with each other in the direction substantially perpendicular to the rotation axis $L_1$ of the driving shaft of the brush head, and a movement gap is existed between the two facets parallel with each other and the second driving portion 371A of the driving wheel. The movement gap ensures that the second driving portion 371A of the driving wheel and the second driven portion 343 of the driven wheel of the brush disc may simply have transmission without redundant interference, and the parallel faces of the two facets parallel with each other are tangential to the second driving portion 371A of the driving wheel, when the second driving portion 371A of the driving wheel drives the second brush disc 34 to reciprocally rotate around the rotation axis $L_2$ of the brush disc. Certainly, the driving portion of the driving wheel may also be designed as cylindrical, as shown in FIG. 12B, wherein the components corresponding to that of FIG. 12A are donated with letter B instead of letter A. and their repeated description will be omitted here. Apparently, the combination structure of the second driving portion 371A of the driving wheel and the second driven portion 343 of the driven wheel of the brush disc may achieve the same assembly flexibility as the combination structure of the driving portion 271 of the driving wheel and the driven portion 243 of the driven wheel of the brush disc in the first embodiment. The second driven portion 343 of the driven wheel of the brush disc may be assembled to a region where the second driving portion 371A of the driving wheel is distributed by passing across the rotation axis of the second driving wheel 37A along the rotation axis $L_2$ of the brush disc from a side opposite to the side of the second driving portion 371A of the driving wheel with respect to the center (i.e., the rotation axis of the second driving wheel 37A), so that the second driven portion 343 of the driven wheel of the brush disc and the second driving portion 371A of the driving wheel cooperate with each other properly. As compared with the single conical tooth-groove structure of the first embodiment, such a structure has a relatively loose requirement for the center distance of the engagement, because the mismatch error between the sphere or cylinder and the facets merely changes the rotational angle, but has less impact on the noise, transmission wear and rotation efficiency. Similarly, the second brush disc 34 is arranged correspondingly with a second rotary surface 342 of the brush disc, the second protrusion of the brush disc 345, a second hollow region 341 of the brush disc, and a second lower wall 344 of the hollow region of the brush disc. The cooperation of the above mentioned second brush disc, the housing of the brush head 22, the second driving shaft of the brush head 36A and the second driving wheel 37A is similar to the cooperation of the brush disc 24, the housing of the brush head 22, the driving shaft of the brush head 26 and the driving wheel 27, and their repeated description is omitted here.

Furthermore, merely one central through hole or top hole may be provided in the housing of the brush head 22 to cooperate with the driving shaft of the brush head 26, and the top hole may be a blind hole or a through hole which is used to restrain the reciprocal rotation of the driving shaft of the brush head 26 around the rotation axis $L_1$ of the driving shaft of the brush head in the hole. The above corresponding variations do not go beyond the scope of the present invention.

Figure 14:
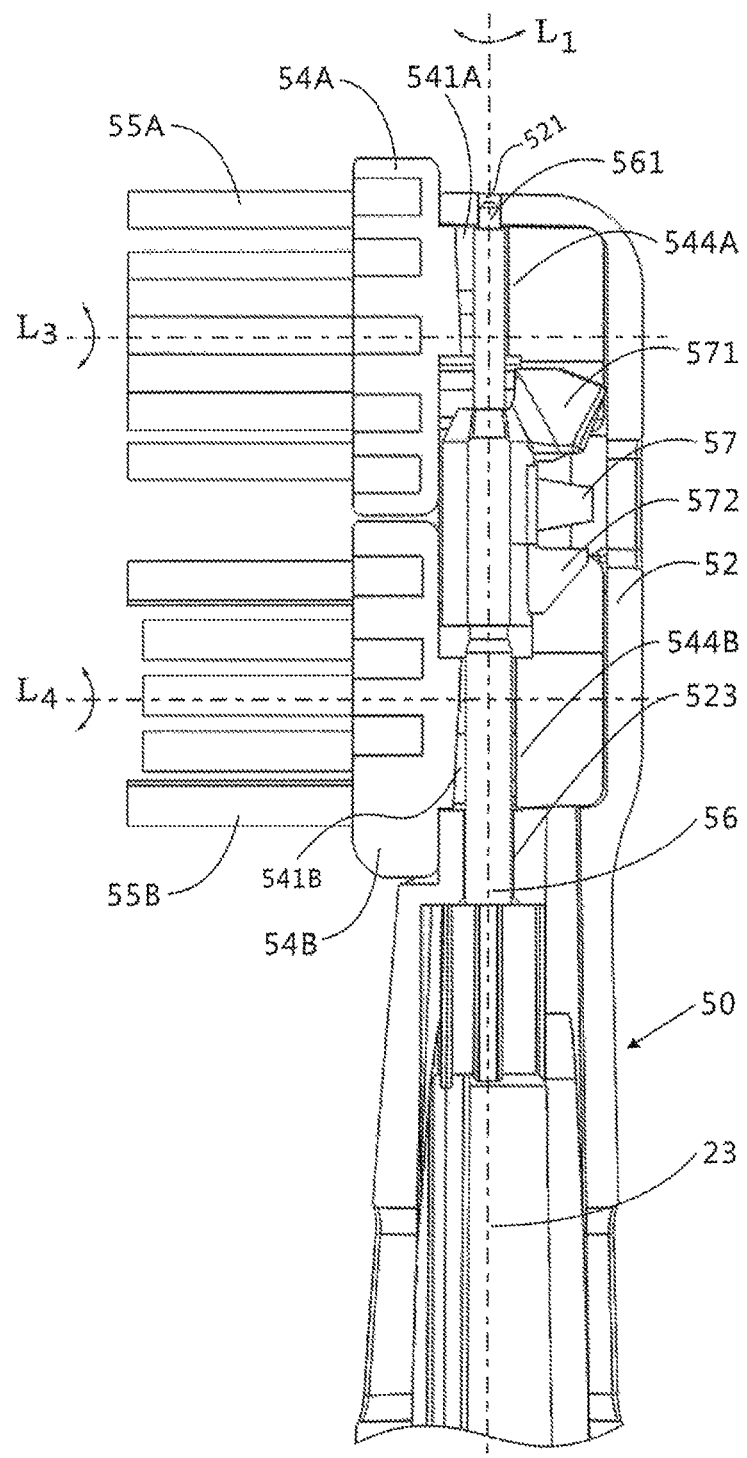
FIG. 14 is a sectional view of the brush head of the electric toothbrush according to the third embodiment of the present invention, in which the brush head have two brush discs.
Figure 15:
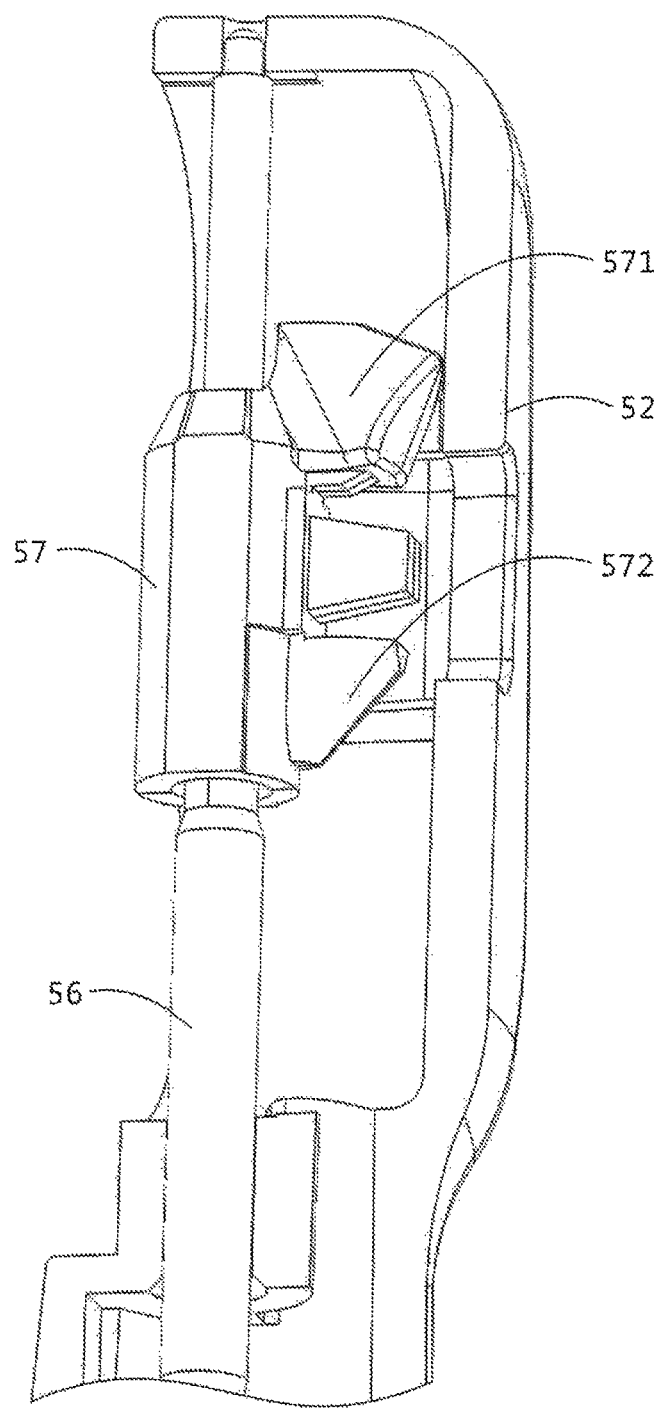
FIG. 15 is an assembly sectional view of the driving wheel of the brush head, driving shaft of the brush head and housing of the brush head as shown in FIG. 14.

The present invention also relates to a brush head having two brush discs. Referring to FIGS. 14 and 15, in the third embodiment, the brush head 50 having two brush discs is detachably assembled onto the handle 1 and includes an interface (or port) of the brush head 21, a housing of the brush head 52 of the brush head having two brush discs, a coupling of the brush head 23, a first brush disc 54A, a second brush disc 54B, a first cleaning element 55A, a second cleaning element 55B, a driving shaft 56 of the brush head having two brush discs, and a driving wheel 57 of the brush head having two brush discs. The brush head having two brush discs 50 is detachably assembled onto the handle 1 through the interface of the brush head 21. The driving shaft of the handle 11 rotates reciprocally around the rotation axis $L_1$ of the driving shaft of the brush head. The driving shaft of the handle 11 is inserted into a lower end of the coupling of the brush head 23. If the shape of the cooperation region of the driving shaft of the handle 11 with the coupling of the brush head 23 (for example, utilizing a tight fit with facets) is properly designed, the driving shaft of the handle 11 drives the coupling of the brush head 23 to reciprocally rotate around the rotation axis $L_1$ of the driving shaft of the brush head. The driving shaft 56 of the brush head having two brush discs is tightly inserted into an upper end of the coupling of the brush head 23. If the shape of the cooperation region of the driving shaft 56 of the brush head having two brush discs with the coupling of the brush head 23 (for example, the driving shaft 56 of the brush head having two brush discs is knurled partially) is properly designed, it is possible that the driving shaft 56 of the brush head having two brush discs and the coupling of the brush head 23 are coupled together immovably, and then have the same reciprocal rotation axis which is the rotation axis $L_1$ of the driving shaft of the brush head, that is, both the driving shaft 56 of the brush head having two brush discs and the coupling of the brush head 23 rotate reciprocally around the rotation axis $L_1$ of the driving shaft of the brush head. The driving shaft 56 of the brush head having two brush discs passes through a central through hole 523 of the housing of the brush head and may rotate freely in the central through hole 523 of the housing of the brush head in a reciprocal manner. Such cooperation is a typical movable shaft-hole cooperation in the project. The driving shaft 56 of the brush head having two brush discs is tightly coupled with the driving wheel 57 of the brush head having two brush discs above the central through hole 523 of the housing of the brush head 52 of the brush head having two brush discs. The driving wheel 57 of the brush head having two brush discs is arranged with a through hole 572 of the driving wheel of the brush head having two brush discs. A portion of the driving shaft 56 of the brush head having two brush discs may pass through the through hole 572 of the driving wheel of the brush head having two brush discs. After the driving shaft of the brush head 56 passes through the through hole 572 of the driving wheel of the brush head having two brush discs, the cooperation region 563 (not shown) of the driving shaft 56 of the brush head having two brush discs with the driving wheel 57 of the brush head having two brush discs enters into the through hole 572 of the driving wheel of the brush head having two brush discs, and the cooperation region 563 has such a shape that the driving shaft 56 of the brush head having two brush discs and the driving wheel 57 of the brush head having two brush discs are immovably fixedly coupled together. Above the driving wheel 57 of the brush head having two brush discs, the driving shaft 56 of the brush head having two brush discs passes through a hollow region 541A of the first brush disc of the brush head having two brush disc; and below the driving wheel 57 of the brush head having two brush discs, the driving shaft 56 of the brush head having two brush discs passes through a hollow region 541B of the second brush disc of the brush head having two brush discs. The first brush disc 54A and the second brush disc 54B may freely rotate around respective rotation axis $L_3$ of the brush discc 54A, rotation axis $L_4$ of the brush disc 54B in a reciprocal manner without interference from the driving shaft 56 of the brush head having two brush discs. Above the hollow region 541A of the first brush disc of the brush head having two brush discs, the top end 561 of the driving shaft of the brush head having two brush discs is inserted into the top hole 521 of the housing of the brush head having two brush discs and may freely rotate around the rotation axis $L_1$ of the driving shaft of the brush head in a reciprocal manner with respect to the top hole 521 of the housing of the brush head having two brush discs. The first brush disc 54A and the second brush disc 54B are respectively arranged with a first cleaning element 55A and a second cleaning element 55B thereon. The top hole 521 of the housing of the brush head having two brush discs and the central through hole 523 of the housing of the brush head having two brush discs are centrally distributed, that is, the centerlines of the two holes are on the same straight line and are on the same straight line with the rotation axis $L_1$ of the driving shaft of the brush head.

The first brush disc 54A and the second brush disc 54B are respectively provided with a first protrusion of the brush disc and a second protrusion of the brush disc, as well as the corresponding hollow region 541A of the first brush disc and the corresponding hollow region 541B of the second brush disc. The above features, functions, and the cooperation of the driving shaft 56 of the brush head having two brush discs are the same as the features, functions, and the cooperation of the driving shaft of the brush head 26 of the previously mentioned single brush disc 24, and the repeated description is omitted here.

In this embodiment, the driving wheel 57 of the brush head having two brush discs is arranged provided with a first driving portion 571 of the driving wheel and a second driving portion 572 of the driving wheel. As described above, the first driving portion 571 of the driving wheel and the second driving portion 572 of the driving wheel may be the single conical tooth of a bevel gear, a sphere or cylinder. The first driving portion 571 of the driving wheel of the brush head having two brush discs drives the driven portion of the first driven wheel of the brush disc, so that the first brush disc reciprocally rotates around the rotation axis $L_3$ of the first brush disc. The second driving portion 572 of the driving wheel of the brush head having two brush discs drives the driven portion of the corresponding second driven wheel of the brush disc, so that the second brush disc reciprocally rotates around the rotation axis $L_4$ of the second brush disc. The driven portion of the first driven wheel of the brush disc is arranged adjacent to the lower side of the first protrusion of the brush disc of the second brush disc. The driven portion of the second driven wheel of the brush disc is arranged adjacent to the upper side of the second protrusion of the brush disc of the first brush disc. The first brush disc 54A and the second brush disc 54B always rotate in opposite directions around respective rotation axis $L_3$, $L_4$, for example, at a certain time, the first brush disc 54A rotates counterclockwise around the rotation axis $L_3$ of the first brush disc, while the second brush disc 54B rotates clockwise around the rotation axis $L_4$ of the second brush disc.

Based on above explanation, the first brush disc 54A and the second brush disc 54B of the brush head having two brush discs 50 have rotation axis $L_3$, $L_4$ parallel with each other and always rotate in opposite directions around respective rotation axis $L_3$, $L_4$. The first brush disc 54A and the second brush disc 54B are respectively arranged with protrusions of the brush disc along respective rotation axis $L_3$, $L_4$ of the brush discs toward the direction away from respective cleaning elements 55A, 55B. The first brush disc 54A and the second brush disc 54B are arranged with respective driven portions of the driven wheel on the regions of the protrusions of the brush disc close to each other. The driving shaft 56 of the brush head having two brush discs is equipped with the driving wheel 57 of the brush head having two brush discs which is immovable with respect to the driving shaft 56 of the brush head having two brush discs. The driving wheel 57 of the brush head having two brush discs is arranged with a first driving portion 571 of the driving wheel and a second driving portion 572 of the driving wheel respectively corresponding to the driven portion of the first driven wheel of the brush disc and the driven portion of the second driven wheel of the brush disc. The driving wheel 57 of the brush head having two brush discs and the driven portion of the driven wheel of the brush disc cooperate to move, and the driving shaft 56 of the brush head having two brush discs drives the driving wheel 57 of the brush head having two brush discs to move. The driving wheel 57 of the brush head having two brush discs drives the driven portion of the driven wheel to move, in such a way that the first brush disc 54A and the second brush disc 54B move, and the first brush disc 54A and the second brush disc 54B drive respective cleaning elements 55A, 55B to move, thus the cleaning effect is achieved. Apparently, the brush head having two brush discs 50 may also be provided with two driving wheels of the brush head which are respectively arranged at lower sides of the respective protrusions of the brush disc of the first brush disc 54A and the second brush disc 54B away from the top of the brush head. The first brush disc 54A and the second brush disc 54B have their respective driven portions of the driven wheel arranged at lower sides of their respective protrusions of the brush disc. As a result, the first brush disc 54A and the second brush disc 54B always rotate in the same direction around their respective rotation axis $L_3$, $L_4$. The variations do not go beyond the scope of the present invention.

The driving shaft 56 of the brush head having two brush discs passes through or enters into the hollow region 541B of the second brush disc of the brush head having two brush discs and the hollow region 541A of the first brush disc of the brush head having two brush discs, and is restrained within the housing of the brush head 52 of the brush head having two brush discs 50 by the top hole 521 and/or the central through hole 523 of the housing of the brush head 52 to rotates reciprocally around about the rotation axis $L_1$ of the driving shaft of the brush head. The driving shaft 56 of the brush head having two brush discs restricts the movement of the first brush disc 54A and the second brush disc 54B along their respective rotation axis $L_3$, $L_4$ of the brush disc toward the direction of cleaning elements 55A, 55B. When the driving shaft 56 of the brush head having two brush discs is not installed or when the driving shaft 56 is damaged, the first brush disc 54A and the second brush disc 54B cannot achieve the reciprocating rotary movement. The recess region of the head of the housing of the brush head of the brush head having two brush discs 50 restricts the movements of the first protrusion of the brush disc and the second protrusion of the brush disc in the direction perpendicular to the rotation axis $L_3$ of the first brush disc or to the rotation axis $L_4$ of the second brush disc, that is, the housing of the brush head 52 of the brush head having two brush discs 50 restricts the movement of the first brush disc 54A and the second brush disc 54B along the direction perpendicular to their respective rotation axis $L_3$, $L_4$ of the brush disc, wherein the housing of the brush head 52 of the brush head having two brush discs 50 is a stationary part. Due to the fact that the housing of the brush head 52 of the brush head having two brush discs 50 includes the first protrusion of the brush disc and the second protrusion of the brush disc which are in motion, the human body's oral tissue can not make contact with the first moving protrusion of the brush disc and second moving protrusion of the brush disc, so as to ensure that the first brush disc 54A and the second brush disc 54B will not harm the oral tissue during movement. Obviously, the brush head of the present invention may further comprise more than two brush discs, and the structure thereof is essentially similar to that structure above stated. These variations do not go beyond the scope of the present invention.

What is claimed is:

1. A reciprocally rotatable brush head, comprising:
    an interface of the brush head (21) detachably connected with a handle (1), a housing of the brush head (22), a driving shaft of the brush head (26), a coupling of the brush head (23) that couples a driving shaft of the handle (11) with the driving shaft of the brush head (26), at least one brush disc (24), a cleaning element (25) distributed on the brush disc, and a driving wheel (27) tightly coupled with the driving shaft of the brush head (26);
    wherein the housing of the brush head (22) is provided with a top hole (221) and a central through hole (223), the top hole (221) and the central through hole (223) are centrally distributed, the rotation axis ($L_1$) of the driving shaft of the brush head and the center line of the top hole (221) and the central through hole (223) are on the same straight line, the driving shaft of the brush head (26) passes through the central through hole (223) of the housing of the brush head, the driving shaft of the brush head (26) can rotate freely in the top hole (221) and the central through hole (223) of the housing of the brush head (22) in a reciprocal manner and is restrained within the housing of the brush head (22) by the top hole (221) and the central through hole (223) so as to rotate reciprocally around a rotation axis ($L_1$) of the driving shaft of the brush head;
    the driving wheel (27) is arranged with a through hole of the driving wheel (272, 372A, 372B), a portion of the driving shaft of the brush head passes through the through holes of the driving wheel (272, 372A, 372B), and after the portion of the driving shaft of the brush head pass through the through hole of the driving wheel (272, 372A, 372B), a cooperation region of the driving shaft of the brush head and the driving wheel enters into the through holes of the driving wheel (272, 372A, 372B), the cooperation region having such a shape that the driving shaft of the brush head (26) and the driving wheel (27) are immovably fixedly coupled together;
    the brush disc (24) is arranged with a protrusion of the brush disc (245) toward a direction away from the cleaning element (25) along a rotation axis ($L_2$) of the brush disc, the protrusion of the brush disc (245) is arranged with a driven portion (243) of a driven wheel of the brush disc matching with a driving portion (271) of the driving wheel, the protrusion of the brush disc (245) is provided with a hollow region of the brush disc (241) along the rotation axis ($L_1$) of the driving shaft of the brush head, and the driving shaft of the brush head (26) passes through or enters into the hollow region of the brush disc (241), the driving shaft of the brush head (26) restricts the movement of the brush disc (24) along the rotation axis ($L_2$) of the brush disc toward the cleaning element (25), and when the driving shaft of the brush head (26) is not installed or is damaged, the brush disc (24) does not perform reciprocating rotary movement.

2. The reciprocally rotatable brush head according to claim 1, wherein the top hole (221) comprises a blind hole or a through hole.

3. The reciprocally rotatable brush head according to claim 2, wherein the driving wheel (27) is provided with a driving portion (271) of the driving wheel located at a side away from the cleaning element (25) with respect to the rotation axis ($L_1$) of the driving shaft of the brush head which is a centerline, and the rotation axis ($L_1$) of the driving shaft of the brush head and the rotation axis ($L_2$) of the brush disc are substantially perpendicular to each other, such that the driven portion (243) of the driven wheel of the brush disc is properly fitted to the driving portion (271) of the driving wheel by passing across the rotation axis ($L_1$) of the driving shaft of the brush head along the rotation axis ($L_2$) of the brush disc in a direction from the cleaning element (25) to the driving wheel (27) from a position away from the driving wheel (27).

4. The reciprocally rotatable brush head according to claim 2, wherein the driving portion (271) of the driving wheel is a single conical tooth of a bevel gear which is arranged along the rotation axis of the brush disc ($L_2$) in a direction away from the cleaning element (25), and the driven portion (243) of the driven wheel of the brush disc matching with the driving portion (271) of the driving wheel is arranged on the protrusion of the brush disc (245) toward a direction away from the cleaning element (25), the driven portion (243) of the driven wheel of the brush disc is a single tooth groove structure that matches the single conical tooth on the driving wheel (27), the single tooth groove structure is formed by two opposite tooth form faces of the same bevel gear.

5. The reciprocally rotatable brush head according to claim 2, wherein the driving wheel (37) is provided with a generally spherical or cylindrical driving portion (371A, 371B) of the driving wheel, the driven portion (343) of the driven wheel of the brush disc is provided with two facets parallel with each other in a direction substantially perpendicular to the rotation axis ($L_1$) of the driving shaft of the brush head, there is a movement gap between the two facets parallel with each other and the driving portion (371A, 371B) of the driving wheel, and the parallel faces of the two facets parallel with each other are tangential to the driving portion (371A, 371B) of the driving wheel.

6. The reciprocally rotatable brush head according to claim 2, wherein the driving shaft of the brush head is made of metal.

7. The reciprocally rotatable brush head according to claim 2, wherein a head of the housing of the brush head (22) further comprises a recess region (224) that restricts a movement of the protrusion of the brush disc (245) in a direction perpendicular to the rotation axis ($L_2$) of the brush disc, that is, the housing of the brush head (22) restricts a movement of the brush disc (24) in the direction perpendicular to the rotation axis ($L_2$) of the brush disc.

8. The reciprocally rotatable brush head according to claim 2, wherein the protrusion of the brush disc (245, 345) is arranged with a rotary surface of the brush disc (242, 342), a side of a recess region (224) of the head of the housing of the brush head is arranged with an inner surface (222) of the housing of the brush head, and the rotary surface of the brush disc (242, 342) is an entire or part of a cylindrical lateral surface when the rotation axis ($L_2$) of the brush disc is its longitudinal axis, or an entire or part of a conical lateral surface when the rotation axis ($L_2$) of the brush disc is its longitudinal axis; the inner surface (222) of the housing of the brush head is an entire or part of a cylindrical lateral surface when the rotation axis of the brush disc ($L_2$) is its longitudinal axis, or an entire or part of a conical lateral surface when the rotation axis of the brush disc ($L_2$) is its longitudinal axis.

9. The reciprocally rotatable brush head according to claim 2, wherein the brush head (50) comprises two brush discs, that is, a first brush disc (54A) and a second brush disc (54B), the first and second brush discs have a same rotation direction or an opposite rotation direction, the first brush disc (54A) and the second brush disc (54B) each comprise protrusions of the brush disc which are arranged with driven portions of the driven wheel of the brush disc matching the corresponding driving portions (571, 572) of the driving wheel and hollow regions of the brush disc (541A, 541B) in the direction of the rotation axis ($L_1$) of the driving shaft of the brush head.

10. The reciprocally rotatable brush head according to claim 9, wherein the driving shaft of the brush head (56) having two brush discs passes through or enters into the hollow regions of the brush disc (541A and 541B) of the first and second brush discs, and is restrained in the housing of the brush head (52) of the brush head (50) having two brush disc by a top hole (521) and a central through hole (523) of the housing of the brush head (52) so as to rotate reciprocally around the rotation axis ($L_1$) of the driving shaft of the brush head.

11. The reciprocally rotatable brush head according to claim 1, wherein the driving wheel (27) is provided with a driving portion (271) of the driving wheel located at a side away from the cleaning element (25) with respect to the rotation axis ($L_1$) of the driving shaft of the brush head which is a centerline, and the rotation axis ($L_1$) of the driving shaft of the brush head and the rotation axis ($L_2$) of the brush disc are substantially perpendicular to each other, such that the driven portion (243) of the driven wheel of the brush disc is properly fitted to the driving portion (271) of the driving wheel by passing across the rotation axis ($L_1$) of the driving shaft of the brush head along the rotation axis ($L_2$) of the brush disc in a direction from the cleaning element (25) to the driving wheel (27) from a position away from the driving wheel (27).

12. The reciprocally rotatable brush head according to claim 11, wherein a portion of the driving shaft of the brush head (26) contained in the hollow region of the brush disc (241) has a length upward along the rotation axis ($L_1$) of the driving shaft of the brush head, the length is greater than a distance by which the driving wheel (27) disengages from the driven portion (243) of the driven wheel of the brush disc.

13. The reciprocally rotatable brush head according to claim 1, wherein the driving portion (271) of the driving wheel is a single conical tooth of a bevel gear which is arranged along the rotation axis of the brush disc ($L_2$) in a direction away from the cleaning element (25), and the driven portion (243) of the driven wheel of the brush disc matching with the driving portion (271) of the driving wheel is arranged on the protrusion of the brush disc (245) toward a direction away from the cleaning element (25), the driven portion (243) of the driven wheel of the brush disc is a single tooth groove structure that matches the single conical tooth on the driving wheel (27), the single tooth groove structure is formed by two opposite tooth form faces of the same bevel gear.

14. The reciprocally rotatable brush head according to claim 13, wherein a portion of the driving shaft of the brush head (26) contained in the hollow region of the brush disc (241) has a length upward along the rotation axis ($L_1$) of the driving shaft of the brush head, the length is greater than a distance by which the driving wheel (27) disengages from the driven portion (243) of the driven wheel of the brush disc.

15. The reciprocally rotatable brush head according to claim 1, wherein the driving wheel (37) is provided with a generally spherical or cylindrical driving portion (371A, 371B) of the driving wheel, the driven portion (343) of the driven wheel of the brush disc is provided with two facets parallel with each other in a direction substantially perpendicular to the rotation axis ($L_1$) of the driving shaft of the brush head, there is a movement gap between the two facets parallel with each other and the driving portion (371A, 371B) of the driving wheel, and the parallel faces of the two facets parallel with each other are tangential to the driving portion (371A, 371B) of the driving wheel.

16. The reciprocally rotatable brush head according to claim 1, wherein the driving shaft of the brush head is made of metal.

17. The reciprocally rotatable brush head according to claim 1, wherein a head of the housing of the brush head (22) further comprises a recess region (224) that restricts a movement of the protrusion of the brush disc (245) in a direction perpendicular to the rotation axis ($L_2$) of the brush disc, that is, the housing of the brush head (22) restricts a movement of the brush disc (24) in the direction perpendicular to the rotation axis ($L_2$) of the brush disc.

18. The reciprocally rotatable brush head according to claim 1, wherein the protrusion of the brush disc (245, 345) is arranged with a rotary surface of the brush disc (242, 342), a side of a recess region (224) of the head of the housing of the brush head is arranged with an inner surface (222) of the housing of the brush head, and the rotary surface of the brush disc (242, 342) is an entire or part of a cylindrical lateral surface when the rotation axis ($L_2$) of the brush disc is its longitudinal axis, or an entire or part of a conical lateral surface when the rotation axis ($L_2$) of the brush disc is its longitudinal axis; the inner surface (222) of the housing of the brush head is an entire or part of a cylindrical lateral surface when the rotation axis of the brush disc ($L_2$) is its longitudinal axis, or an entire or part of a conical lateral surface when the rotation axis of the brush disc ($L_2$) is its longitudinal axis.

19. The reciprocally rotatable brush head according to claim 1, wherein the brush head (50) comprises two brush discs, that is, a first brush disc (54A) and a second brush disc (54B), the first and second brush discs have a same rotation direction or an opposite rotation direction, the first brush disc (54A) and the second brush disc (54B) each comprise protrusions of the brush disc which are arranged with driven portions of the driven wheel of the brush disc matching the corresponding driving portions (571, 572) of the driving wheel and hollow regions of the brush disc (541A, 541B) in the direction of the rotation axis ($L_1$) of the driving shaft of the brush head.

20. The reciprocally rotatable brush head according to claim 19, wherein the driving shaft of the brush head (56) having two brush discs passes through or enters into the hollow regions of the brush disc (541A and 541B) of the first and second brush discs, and is restrained in the housing of the brush head (52) of the brush head (50) having two brush disc by a top hole (521) and a central through hole (523) of the housing of the brush head (52) so as to rotate reciprocally around the rotation axis ($L_1$) of the driving shaft of the brush head.

21. A reciprocally rotatable brush head, comprising:

an interface of the brush head (21) detachably connected with a handle (1), a housing of the brush head (22), a driving shaft of the brush head (26), a coupling of the brush head (23) that couples a driving shaft of the handle (11) with the driving shaft of the brush head (26), at least one brush disc (24), a cleaning element (25) distributed on the brush disc, and a driving wheel (27) tightly coupled with the driving shaft of the brush head (26);

wherein the housing of the brush head (22) is provided with a top hole (221) or a central through hole (223), the top hole (221) or the central through hole (223) is centrally distributed, the rotation axis ($L_1$) of the driving shaft of the brush head and the center line of the top hole (221) or the central through hole (223) are on the same straight line, the driving shaft of the brush head (26) passes through the central through hole (223) of the housing of the brush head, the driving shaft of the brush head (26) can rotate freely in the top hole (221) or the central through hole (223) of the housing of the brush head (22) in a reciprocal manner and is restrained within the housing of the brush head (22) by the top hole (221) or the central through hole (223) so as to rotate reciprocally around a rotation axis ($L_1$) of the driving shaft of the brush head;

the driving wheel (27) is arranged with a through hole of the driving wheel (272, 372A, 372B), a portion of the driving shaft of the brush head passes through the through holes of the driving wheel (272, 372A, 372B), and after the portion of the driving shaft of the brush head pass through the through hole of the driving wheel (272, 372A, 372B), a cooperation region of the driving shaft of the brush head and the driving wheel enters into the through holes of the driving wheel (272, 372A, 372B), the cooperation region having such a shape that the driving shaft of the brush head (26) and the driving wheel (27) are immovably fixedly coupled together;

the brush disc (24) is arranged with a protrusion of the brush disc (245) toward a direction away from the cleaning element (25) along a rotation axis ($L_2$) of the brush disc, the protrusion of the brush disc (245) is arranged with a driven portion (243) of a driven wheel of the brush disc matching with a driving portion (271) of the driving wheel, the protrusion of the brush disc (245) is provided with a hollow region of the brush disc (241) along the rotation axis ($L_1$) of the driving shaft of the brush head, and the driving shaft of the brush head (26) passes through or enters into the hollow region of the brush disc (241), the driving shaft of the brush head (26) restricts the movement of the brush disc (24) along the rotation axis ($L_2$) of the brush disc toward the cleaning element (25), and when the driving shaft of the brush head (26) is not installed or is damaged, the brush disc (24) does not perform reciprocating rotary movement.

22. The reciprocally rotatable brush head according to claim 21, wherein the top hole (221) comprises a blind hole or a through hole.

23. The reciprocally rotatable brush head according to claim 22, wherein the driving wheel (27) is provided with a driving portion (271) of the driving wheel located at a side away from the cleaning element (25) with respect to the rotation axis (L1) of the driving shaft of the brush head which is a centerline, and the rotation axis (L1) of the driving shaft of the brush head and the rotation axis (L2) of the brush disc are substantially perpendicular to each other, such that the driven portion (243) of the driven wheel of the brush disc is properly fitted to the driving portion (271) of the driving wheel by passing across the rotation axis (L1) of the driving shaft of the brush head along the rotation axis (L2) of the brush disc in a direction from the cleaning element (25) to the driving wheel (27) from a position away from the driving wheel (27).

24. The reciprocally rotatable brush head according to claim 22, wherein the driving portion (271) of the driving wheel is a single conical tooth of a bevel gear which is arranged along the rotation axis of the brush disc (L2) in a direction away from the cleaning element (25), and the driven portion (243) of the driven wheel of the brush disc matching with the driving portion (271) of the driving wheel is arranged on the protrusion of the brush disc (245) toward a direction away from the cleaning element (25), the driven portion (243) of the driven wheel of the brush disc is a single tooth groove structure that matches the single conical tooth on the driving wheel (27), the single tooth groove structure is formed by two opposite tooth form faces of the same bevel gear.

25. The reciprocally rotatable brush head according to claim 22, wherein the driving wheel (37) is provided with a generally spherical or cylindrical driving portion (371A, 371B) of the driving wheel, the driven portion (343) of the driven wheel of the brush disc is provided with two facets parallel with each other in a direction substantially perpendicular to the rotation axis ($L_1$) of the driving shaft of the brush head, there is a movement gap between the two facets parallel with each other and the driving portion (371A, 371B) of the driving wheel, and the parallel faces of the two facets parallel with each other are tangential to the driving portion (371A, 371B) of the driving wheel.

26. The reciprocally rotatable brush head according to claim 22, wherein the driving shaft of the brush head is made of metal.

27. The reciprocally rotatable brush head according to claim 22, wherein a head of the housing of the brush head (22) further comprises a recess region (224) that restricts a movement of the protrusion of the brush disc (245) in a direction perpendicular to the rotation axis ($L_2$) of the brush disc, that is, the housing of the brush head (22) restricts a movement of the brush disc (24) in the direction perpendicular to the rotation axis ($L_2$) of the brush disc.

28. The reciprocally rotatable brush head according to claim 22, wherein the protrusion of the brush disc (245, 345) is arranged with a rotary surface of the brush disc (242, 342), a side of a recess region (224) of the head of the housing of the brush head is arranged with an inner surface (222) of the housing of the brush head, and the rotary surface of the brush disc (242, 342) is an entire or part of a cylindrical lateral surface when the rotation axis ($L_2$) of the brush disc is its longitudinal axis, or an entire or part of a conical lateral surface when the rotation axis ($L_2$) of the brush disc is its longitudinal axis; the inner surface (222) of the housing of the brush head is an entire or part of a cylindrical lateral surface when the rotation axis of the brush disc ($L_2$) is its longitudinal axis, or an entire or part of a conical lateral surface when the rotation axis of the brush disc ($L_2$) is its longitudinal axis.

29. The reciprocally rotatable brush head according to claim 22, wherein the brush head (50) comprises two brush discs, that is, a first brush disc (54A) and a second brush disc (54B), the first and second brush discs have a same rotation direction or an opposite rotation direction, the first brush disc (54A) and the second brush disc (54B) each comprise protrusions of the brush disc which are arranged with driven portions of the driven wheel of the brush disc matching the corresponding driving portions (571, 572) of the driving wheel and hollow regions of the brush disc (541A, 541B) in the direction of the rotation axis ($L_1$) of the driving shaft of the brush head.

30. The reciprocally rotatable brush head according to claim 29, wherein the driving shaft of the brush head (56) having two brush discs passes through or enters into the hollow regions of the brush disc (541A and 541B) of the first and second brush discs, and is restrained in the housing of the brush head (52) of the brush head (50) having two brush disc by a top hole (521) or a central through hole (523) of the housing of the brush head (52) so as to rotate reciprocally around the rotation axis ($L_1$) of the driving shaft of the brush head.

31. The reciprocally rotatable brush head according to claim 21, wherein the driving wheel (27) is provided with a driving portion (271) of the driving wheel located at a side away from the cleaning element (25) with respect to the rotation axis ($L_1$) of the driving shaft of the brush head which is a centerline, and the rotation axis ($L_1$) of the driving shaft of the brush head and the rotation axis ($L_2$) of the brush disc are substantially perpendicular to each other, such that the driven portion (243) of the driven wheel of the brush disc is properly fitted to the driving portion (271) of the driving wheel by passing across the rotation axis ($L_1$) of the driving shaft of the brush head along the rotation axis ($L_2$) of the brush disc in a direction from the cleaning element (25) to the driving wheel (27) from a position away from the driving wheel (27).

32. The reciprocally rotatable brush head according to claim 31, wherein a portion of the driving shaft of the brush head (26) contained in the hollow region of the brush disc (241) has a length upward along the rotation axis ($L_1$) of the driving shaft of the brush head, the length is greater than a distance by which the driving wheel (27) disengages from the driven portion (243) of the driven wheel of the brush disc.

33. The reciprocally rotatable brush head according to claim 21, wherein the driving portion (271) of the driving wheel is a single conical tooth of a bevel gear which is arranged along the rotation axis of the brush disc ($L_2$) in a direction away from the cleaning element (25), and the driven portion (243) of the driven wheel of the brush disc matching with the driving portion (271) of the driving wheel is arranged on the protrusion of the brush disc (245) toward a direction away from the cleaning element (25), the driven portion (243) of the driven wheel of the brush disc is a single tooth groove structure that matches the single conical tooth on the driving wheel (27), the single tooth groove structure is formed by two opposite tooth form faces of the same bevel gear.

34. The reciprocally rotatable brush head according to claim 33, wherein a portion of the driving shaft of the brush head (26) contained in the hollow region of the brush disc (241) has a length upward along the rotation axis ($L_1$) of the driving shaft of the brush head, the length is greater than a distance by which the driving wheel (27) disengages from the driven portion (243) of the driven wheel of the brush disc.

35. The reciprocally rotatable brush head according to claim 21, wherein the driving wheel (37) is provided with a generally spherical or cylindrical driving portion (371A, 371B) of the driving wheel, the driven portion (343) of the driven wheel of the brush disc is provided with two facets parallel with each other in a direction substantially perpendicular to the rotation axis ($L_1$) of the driving shaft of the brush head, there is a movement gap between the two facets parallel with each other and the driving portion (371A, 371B) of the driving wheel, and the parallel faces of the two facets parallel with each other are tangential to the driving portion (371A, 371B) of the driving wheel.

36. The reciprocally rotatable brush head according to claim 21, wherein the driving shaft of the brush head is made of metal.

37. The reciprocally rotatable brush head according to claim 21, wherein a head of the housing of the brush head (22) further comprises a recess region (224) that restricts a movement of the protrusion of the brush disc (245) in a direction perpendicular to the rotation axis ($L_2$) of the brush disc, that is, the housing of the brush head (22) restricts a movement of the brush disc (24) in the direction perpendicular to the rotation axis ($L_2$) of the brush disc.

38. The reciprocally rotatable brush head according to claim 21, wherein the protrusion of the brush disc (245, 345) is arranged with a rotary surface of the brush disc (242, 342), a side of a recess region (224) of the head of the housing of the brush head is arranged with an inner surface (222) of the housing of the brush head, and the rotary surface of the brush disc (242, 342) is an entire or part of a cylindrical lateral surface when the rotation axis ($L_2$) of the brush disc is its longitudinal axis, or an entire or part of a conical lateral surface when the rotation axis ($L_2$) of the brush disc is its longitudinal axis; the inner surface (222) of the housing of the brush head is an entire or part of a cylindrical lateral surface when the rotation axis of the brush disc ($L_2$) is its longitudinal axis, or an entire or part of a conical lateral surface when the rotation axis of the brush disc ($L_2$) is its longitudinal axis.

39. The reciprocally rotatable brush head according to claim 21, wherein the brush head (50) comprises two brush discs, that is, a first brush disc (54A) and a second brush disc (54B), the first and second brush discs have a same rotation direction or an opposite rotation direction, the first brush disc (54A) and the second brush disc (54B) each comprise protrusions of the brush disc which are arranged with driven portions of the driven wheel of the brush disc matching the corresponding driving portions (571, 572) of the driving wheel and hollow regions of the brush disc (541A, 541B) in the direction of the rotation axis ($L_1$) of the driving shaft of the brush head.

40. The reciprocally rotatable brush head according to claim 39, wherein the driving shaft of the brush head (56) having two brush discs passes through or enters into the hollow regions of the brush disc (541A and 541B) of the first and second brush discs, and is restrained in the housing of the brush head (52) of the brush head (50) having two brush disc by a top hole (521) or a central through hole (523) of the housing of the brush head (52) so as to rotate reciprocally around the rotation axis ($L_1$) of the driving shaft of the brush head.

* * * * *